US012076050B2

(12) United States Patent
Fessler et al.

(10) Patent No.: US 12,076,050 B2
(45) Date of Patent: Sep. 3, 2024

(54) SINGLE LEVEL FUSION SYSTEMS AND METHODS OF ASSEMBLY AND USE

(71) Applicant: DUET SPINE HOLDINGS, LLC, Winona Lake, IN (US)

(72) Inventors: Richard G. Fessler, Lake Forest, IL (US); Jon C. Serbousek, Winona Lake, IN (US); Jill A. Serbousek, Winona Lake, IN (US); Jeffrey Nycz, Warsaw, IN (US)

(73) Assignee: DUET SPINE HOLDINGS, LLC, Winona Lake, IN (US)

( * ) Notice: Subject to any disclaimer, the term of this patent is extended or adjusted under 35 U.S.C. 154(b) by 76 days.

(21) Appl. No.: 17/450,099

(22) Filed: Oct. 6, 2021

(65) Prior Publication Data
US 2022/0022921 A1 Jan. 27, 2022

Related U.S. Application Data

(60) Continuation of application No. 15/971,503, filed on May 4, 2018, now abandoned, which is a division of
(Continued)

(51) Int. Cl.
*A61B 17/70* (2006.01)
*A61B 17/00* (2006.01)
(Continued)

(52) U.S. Cl.
CPC ...... *A61B 17/7005* (2013.01); *A61B 17/7002* (2013.01); *A61B 17/7004* (2013.01); *A61B 17/701* (2013.01); *A61B 17/7085* (2013.01); *A61B 17/7091* (2013.01); *A61B 17/888* (2013.01); *A61B 17/8888* (2013.01); *A61B 2017/00526* (2013.01); *A61B 17/70* (2013.01); *A61B 17/7001* (2013.01); *A61B 17/7007* (2013.01); *A61B 17/7032* (2013.01); *A61B 17/7035* (2013.01); *A61B 17/7064* (2013.01);
(Continued)

(58) Field of Classification Search
CPC ............ A61B 17/7005; A61B 17/7085; A61B 17/7091; A61B 17/888
See application file for complete search history.

(56) References Cited

U.S. PATENT DOCUMENTS

| | | | |
|---|---|---|---|
| 7,422,597 B1 * | 9/2008 | Alby | A61B 17/7091 606/301 |
| 2004/0039384 A1 | 2/2004 | Boehm, Jr. | |

(Continued)

OTHER PUBLICATIONS

Extended European Search Report issued in European Patent Application No. 21173781.2, Sep. 27, 2021, 8 pages.

*Primary Examiner* — Nicholas J Plionis
(74) *Attorney, Agent, or Firm* — Heslin Rothenberg Farley & Mesiti P.C.; Jacquelyn A. Graff, Esq.

(57) ABSTRACT

The present invention discloses single level fusion systems and methods of use. The single level fusion systems include a first fastener, a second fastener, and a connector to secure the first fastener to the second fastener. The method of assembling a single level fusion system including obtaining a first fastener, a second fastener, and a connector, securing the first fastener to the connector, and securing the second fastener to the connector. Methods of using the single level fusion systems are also disclosed.

20 Claims, 37 Drawing Sheets

Related U.S. Application Data application No. 15/463,744, filed on Mar. 20, 2017, now Pat. No. 10,517,644, which is a continuation of application No. PCT/US2015/051254, filed on Sep. 21, 2015.

(60) Provisional application No. 62/052,915, filed on Sep. 19, 2014.

(51) Int. Cl.
*A61B 17/86* (2006.01)
*A61B 17/88* (2006.01)

(52) U.S. Cl.
CPC ....... *A61B 17/8625* (2013.01); *A61B 17/8685* (2013.01)

(56) References Cited

U.S. PATENT DOCUMENTS

| | | |
|---|---|---|
| 2005/0015093 A1 | 1/2005 | Suh |
| 2005/0085813 A1 | 4/2005 | Spitler |
| 2007/0167949 A1* | 7/2007 | Altarac ............... A61B 17/7032 606/104 |
| 2007/0239159 A1* | 10/2007 | Altarac ............... A61B 17/7091 606/86 A |
| 2008/0177306 A1 | 7/2008 | Lanx |
| 2010/0211074 A1 | 8/2010 | Hansson |
| 2010/0268119 A1* | 10/2010 | Morrison ........... A61B 17/8863 600/587 |
| 2014/0046385 A1* | 2/2014 | Asaad ................ A61B 17/8605 606/305 |
| 2021/0113249 A1 | 4/2021 | Shoemaker |

\* cited by examiner

SINGLE LEVEL FUSION SYSTEMS AND METHODS OF ASSEMBLY AND USE

CROSS REFERENCE TO RELATED APPLICATION

This application is a continuation of U.S. application Ser. No. 15/971,503 filed on May 4, 2018, which is a divisional of U.S. application Ser. No. 15/463,744 filed on Mar. 20, 2017, which issued as U.S. Pat. No. 10,517,644 on Dec. 31, 2019 and which claims priority benefit from PCT Application No. PCT/US2015/051254 filed on Sep. 21, 2015, which claimed priority of U.S. provisional application No. 62/052,915 filed Sep. 19, 2014, all of which are incorporated herein by reference in their entireties.

FIELD OF THE INVENTION

The present invention relates generally to general surgery, orthopaedic and neurosurgical implants used for insertion within a patient's vertebrae. More specifically, but not exclusively, the present invention concerns single level fusion systems for implantation into the spine to maintain or re-establish proper spacing and alignment within a patient's spine.

BACKGROUND OF THE INVENTION

Spinal deformities may result from disease, age, or trauma causing destabilization of the spine. To correct destabilization of a patient's spine, posterior fusion device systems may be used. The posterior fusion device systems that are currently available are designed to be applicable to single and multiple level stabilizations. These posterior fusion device systems and the instrumentation used for insertion into a patient's spine are extensive, complicated, and expensive.

SUMMARY OF THE INVENTION

Aspects of the present invention provide single level fusion systems and methods that can maintain or re-establish anatomic spacing within a patient's spine.

In one aspect, provided herein is a single level fusion system, including a first fastener, a second fastener, and a connector to secure the first fastener to the second fastener.

In another aspect, provided herein is a method for assembling a single level fusion system including: obtaining a first fastener, a second fastener, and a connector. The connector includes a first member, a second member, and a locking mechanism coupling the first member and the second member. The method also includes securing the first fastener to the connector and securing the second fastener to the connector.

In yet another aspect, provided herein is a surgical method for inserting a single level fusion system, including exposing the patient's vertebrae. The method may also include obtaining the single level fusion system and inserting a first fastener into a first vertebra. Further, the method may include inserting a second fastener into a second vertebra to the first vertebra and coupling the first fastener and the second fastener.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion.

DETAILED DESCRIPTION FOR CARRYING OUT THE INVENTION

Figure 1:
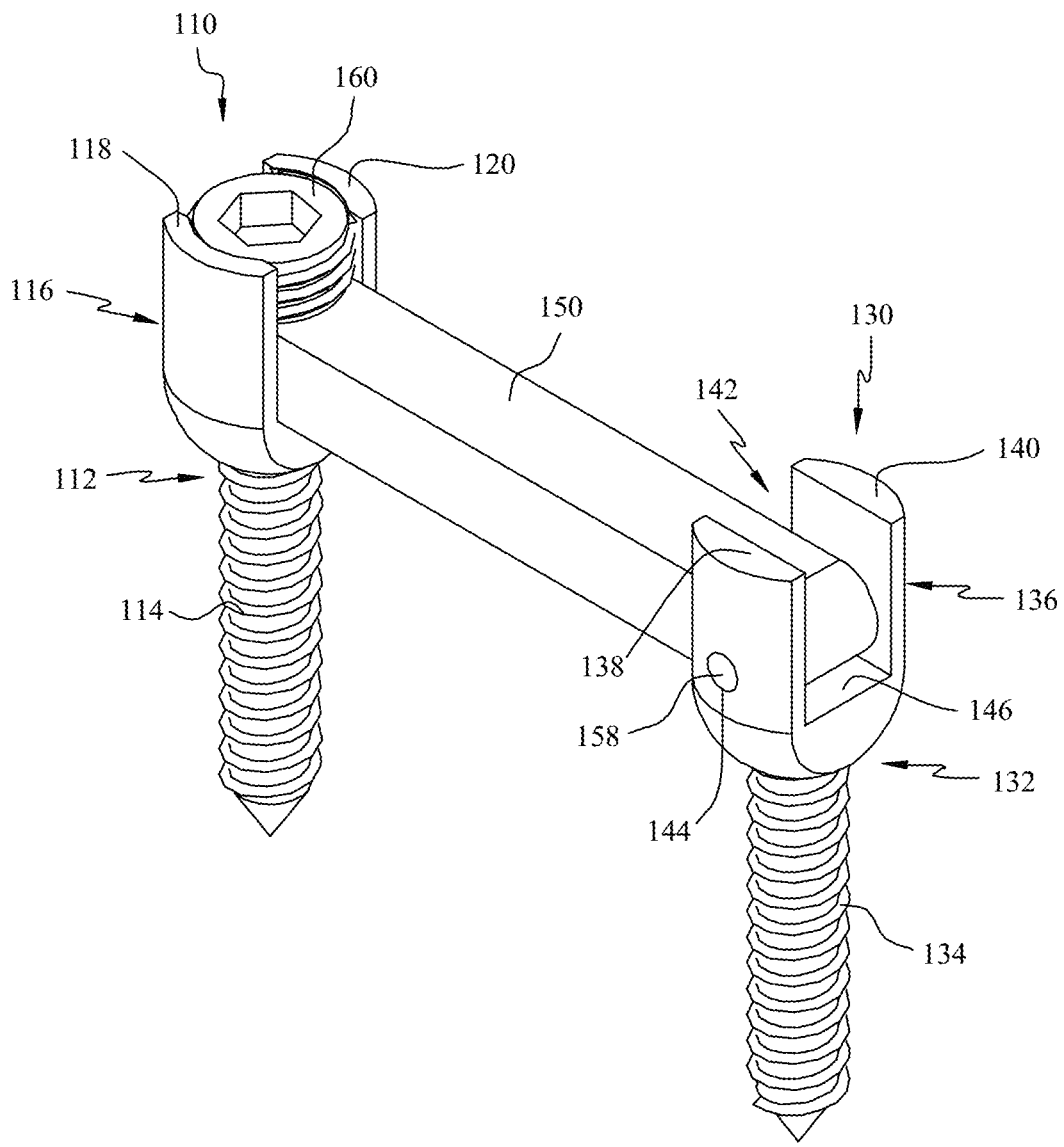
FIG. 1 is a perspective view of a single level fusion system, in accordance with an aspect of the present invention.
Figure 2:
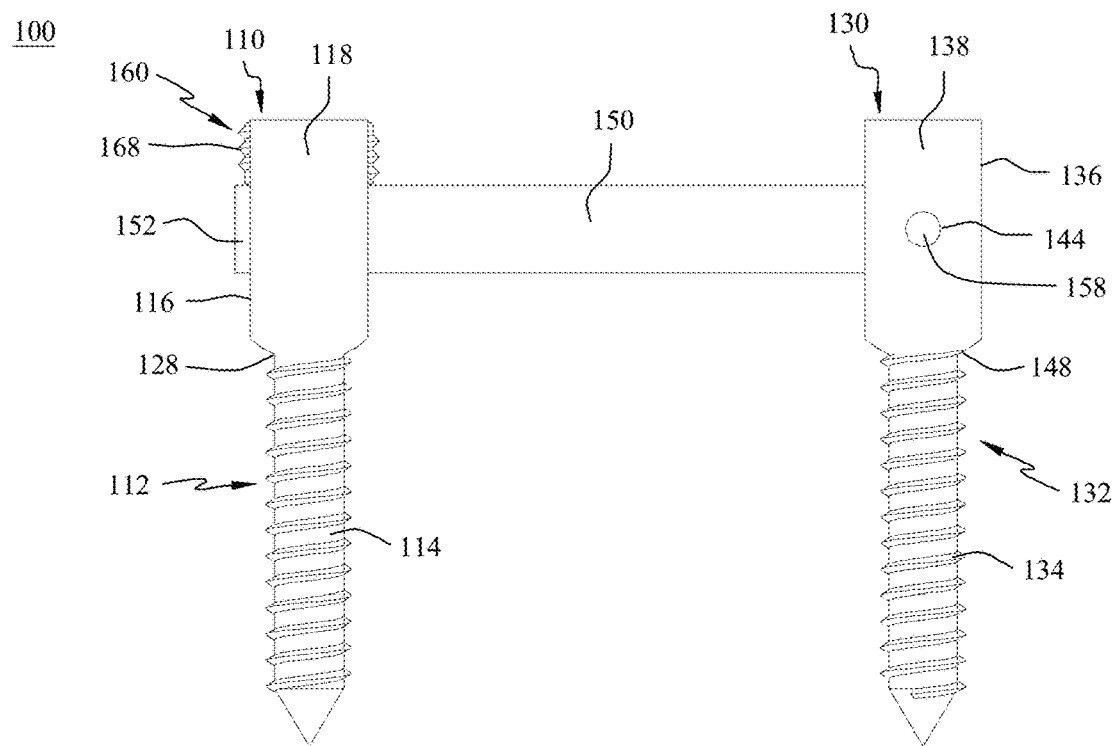
FIG. 2 is a side view of the single level fusion system of FIG. 1, in accordance with an aspect of the present invention.
Figure 3:
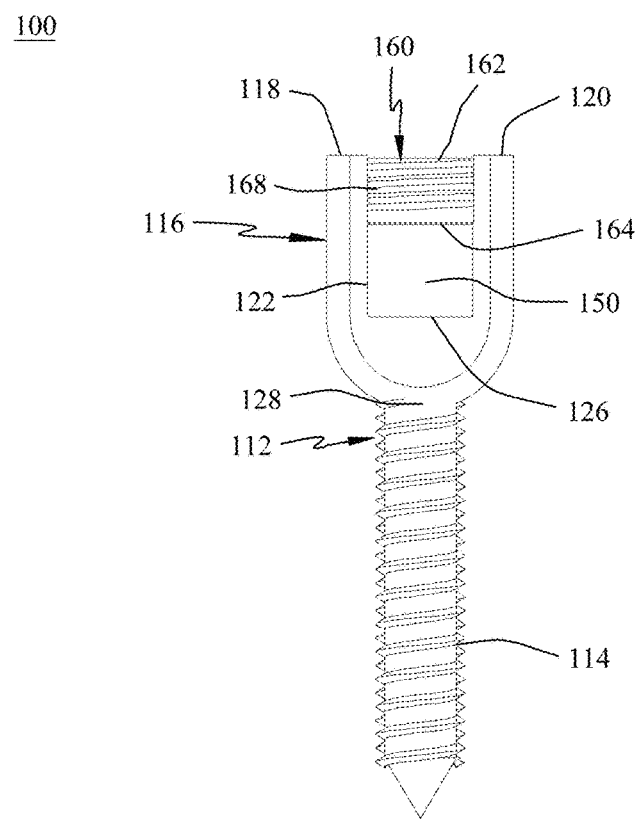
FIG. 3 is an end view of the single level fusion system of FIG. 1, in accordance with an aspect of the present invention.

Generally stated, disclosed herein are single level fusion systems. Further, surgical methods for inserting the single level fusion systems are discussed.

In this detailed description and the following claims, the words proximal, distal, anterior, posterior, medial, lateral, superior, inferior, cephalad and caudally are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure, "cephalad" means a direction toward the head and "caudally" means a direction toward the inferior part of the body.

Referring to the drawings, wherein like reference numerals are used to indicate like or analogous components throughout the several views, and with particular reference to FIGS. 1-5, there is illustrated an exemplary embodiment of a single level fusion system 100. The single level fusion system 100 may include a first fastener assembly 110, a second fastener assembly 130, and an elongate member 150.

Figure 4:
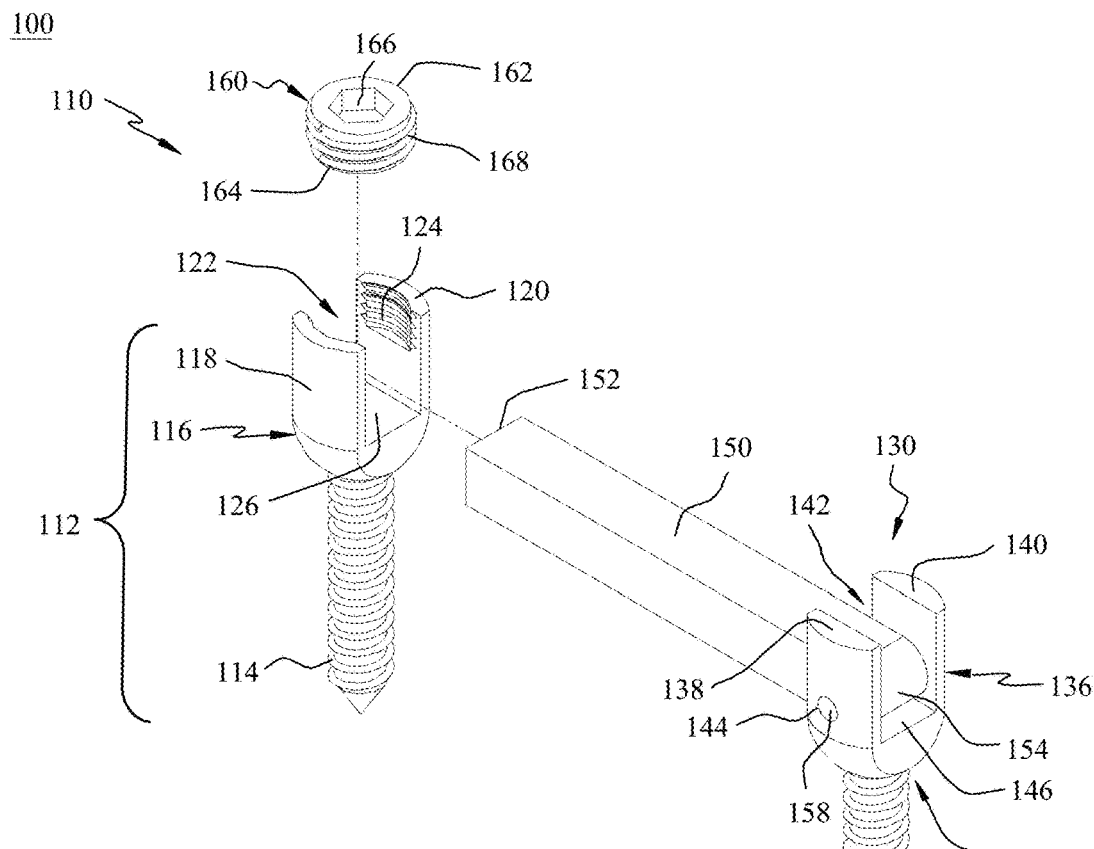
FIG. 4 is a partially exploded first perspective view of the single level fusion system of FIG. 1, in accordance with an aspect of the present invention.
Figure 5:
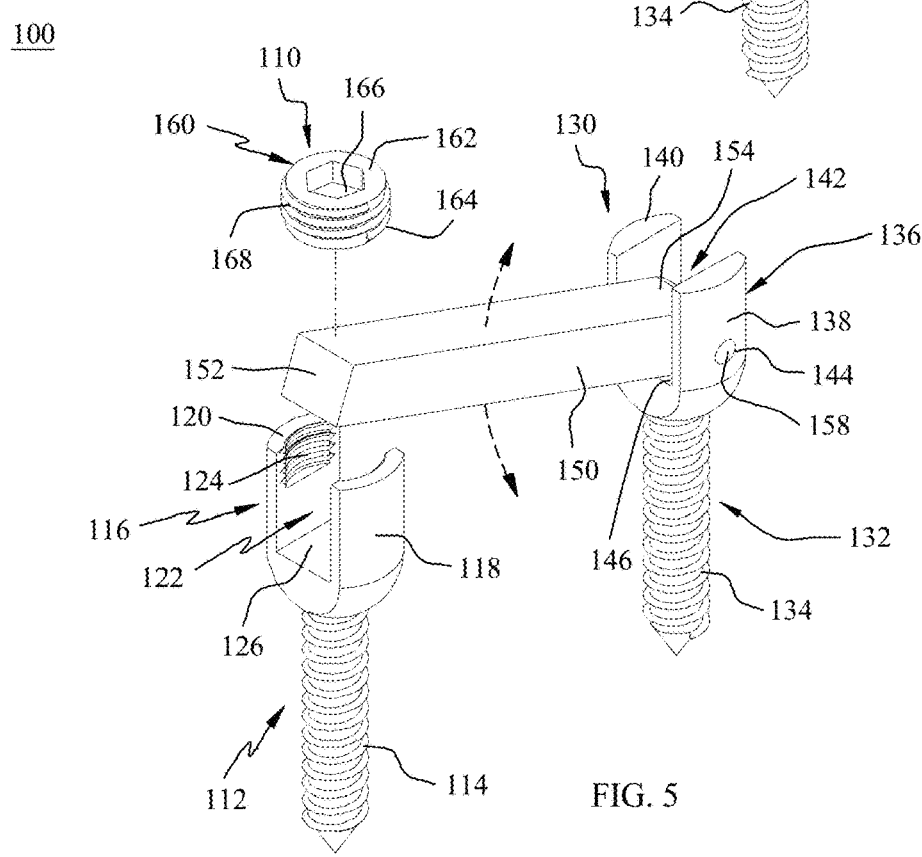
FIG. 5 is a partially exploded second perspective view of the single level fusion system of FIG. 1, in accordance with an aspect of the present invention.

With continued reference to FIGS. 1-5, the first fastener assembly 110 may include a first fastener 112 and a set screw 160. The first fastener 112 may have a shaft 114, a head 116, and a neck 128 connecting the shaft 114 and the head 116. The shaft 114 may be, for example, threaded along its entire length, threaded along only a portion of the length, or non-threaded. As shown in FIGS. 4 and 5, the head 116 may include a first arm 118, a second arm 120, and a passageway 122 extending between the first arm 118 and the second arm 120. The first arm 118 and second arm 120 each have an interior surface formed by the passageway 122. The passageway 122 also forms a base 126 near the bottom of the head 116. The base 126 may be, for example, planar, as shown, or alternatively may be curved concavely or convexly. The first arm 118 and second arm 120 may have, for example, a threaded portion 124 that extends along at least a portion of the interior surface of the first arm 118 and the second arm 120 from the top surface of the first and second arms 118, 120 toward the base 126.

As shown in FIGS. 4 and 5, the set screw 160 may include a top surface 162 and a bottom surface 164. The set screw 160 may also include a tool engagement opening 166 extending into the set screw 160 from the top surface 162 toward the bottom surface 164. In addition, the set screw 160 may include threads 168 on the exterior surface extending from the top surface 162 to the bottom surface 164.

The second fastener assembly 130, as shown in FIGS. 1-2 and 4-5, may include a second fastener 132 and a hinge member 158. The second fastener 132 may have a shaft 134, a head 136, and a neck 148 connecting the shaft 134 and the head 136. The shaft 134 may be, for example, threaded along its entire length, threaded along only a portion of its length, or non-threaded. As shown in FIGS. 4 and 5, the head 136 may include a first arm 138, a second arm 140, and a passageway 142 extending between the first arm 138 and the second arm 140. The first arm 138 and the second arm 140 each have an interior surface formed by the passageway 142. The passageway 142 also forms a base 146 near the bottom of the head 136. The first arm 138 and second arm 140 may, for example, each include an opening 144 extending from the interior surface to an exterior surface of the arms 138, 140.

Although the fasteners shown throughout the present description, such as fasteners 112, 132, are shown as being straight, it is also contemplated that the fasteners may have curved shafts that may be driven into the patient's vertebrae rather than screwed.

As shown in FIGS. 1-2 and 4-5, at least one hinge member 158 may be positioned within the openings 144 in the first arm 138 and the second arm 140. The at least one hinge member 158 may also, for example, pass through the elongate member 150 to secure the elongate member 150 to the second fastener 132.

The elongate member 150 may include a first end 152 and a second end 154, as shown in FIGS. 4 and 5. In one embodiment, it is contemplated that the elongate member 150 may include an opening (not shown) near the second end 154 to receive the at least one hinge member 158. In an alternative embodiment, it is contemplated that the elongate member 150 may include at least one hinge member 158 coupled to the second end 154 of the elongate member 150. Alternative attachment mechanisms, as known by one of ordinary skill in the art, which enable the elongate member 150 to rotate with respect to the second fastener 132 are also contemplated. The system 100 may be implanted by first obtaining a first fastener assembly 110, a second fastener assembly 130, and an elongate member 150. Next, the elongate member 150 may be coupled to the second fastener assembly 130 by inserting the hinge member 158 into the openings 144 in the second fastener 132 to secure the elongate member 150 to the second fastener 132. Then the first fastener 112 and second fastener assembly 130 with the attached elongate member 150 may each be inserted into the desired vertebrae. After insertion of the first fastener 112 and the second fastener 132, the elongate member 150 may be moved into position between the first arm 118 and second arm 120 of the first fastener 112. Next, the set screw 160 may be inserted at least partially to secure the elongate member 150 into the head of the first fastener 112. It may be desirable to only partially insert the set screw 160 to allow for the elongate member 150 to slide within the passageway 122 to enable the surgeon to position the first fastener 112 with respect to the second fastener 132 to maintain or re-establish proper spacing and alignment within the patient's spine. Once the desired position of the first fastener 112 and second fastener 132 is achieved, the set screw 160 may be fully inserted to secure the elongate member 150 in the desired position. Finally, the patient's incision may be closed.

Figure 6:
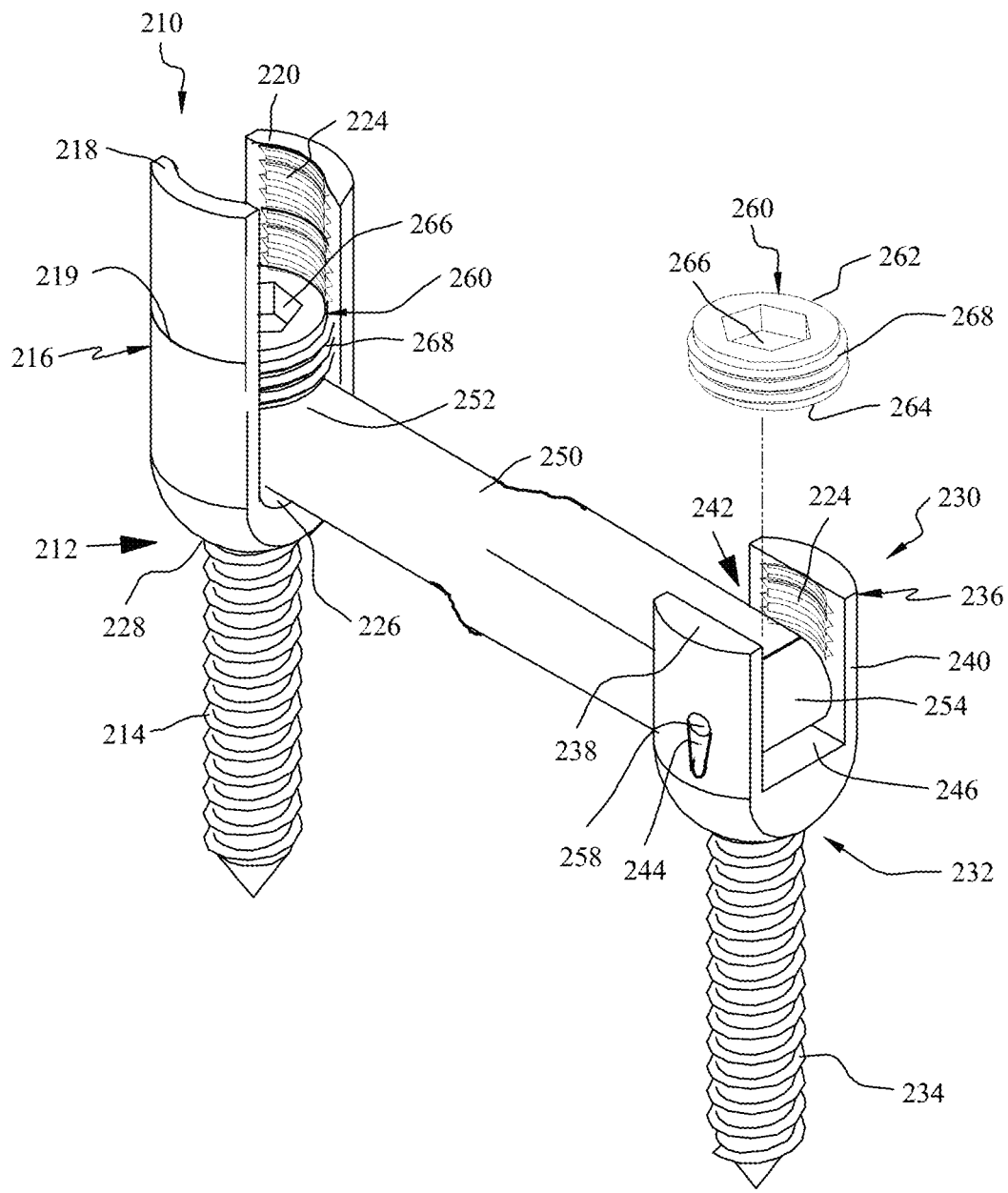
FIG. 6 is a perspective view of another single level fusion system, in accordance with an aspect of the present invention.

Another single level fusion system 200 is shown in FIG. 6. The single level fusion system 200 may include a first fastener assembly 210, a second fastener assembly 230, and an elongate member 250. The first fastener assembly 210 may include a first fastener 212 and a set screw 260. The first fastener 212 may include a shaft 214, a head 216, and a neck 228 connecting the shaft 214 and the head 216. The shaft 214 and neck 228 may be of the type described above with reference to the shaft 114 and neck 128, as described above, which will not be described again here for brevity sake. The head 216 may include a first arm 218, a second arm 220, and a passageway 222 extending between the first arm 218 and the second arm 220. The first arm 218 and second arm 220 each have an interior surface formed by the passageway 222. The passageway 222 also forms a base 226 near the bottom of the head 216. The base 226 may be curved or arced concavely to receive a correspondingly shaped elongate member 250. The first arm 218 and second arm 220 may have, for example, a threaded portion 224 that extends along at least a portion of the interior surface of the first arm 218 and the second arm 220 from the top surface of the first and second arms 218, 220 toward the base 226. The first and second arms 218, 220 may be similar to first and second arms 118, 120, however the first and second arms 218, 220 are longer than the first and second arms 118, 120. The first and second arms 218, 220 may also each include a break off line 219. The break off line 219 provides a guide for shortening the first fastener 212 and the line 219 may be, for example, grooved or non-grooved. The longer arms 218, 220 may provide for a larger head 216 to make it easier to start the insertion of the fastener 212 into the patient. However, it may not be desirable to have a longer head 216 remain in the patient, thus the line 219 provides for a break off point to shorten the arms 218, 220 of the head 216.

The set screw 260 may include a top surface 262, a bottom surface 264, a tool engagement opening 266, and threads 268 of the type described above with references to set screw 160 and the top surface 162, bottom surface 164, tool engagement opening 166, and threads 168, respectively, which will not be described again here for brevity sake.

The second fastener assembly 230 may include a second fastener 232, a set screw 260, and a hinge member 258. The second fastener 232 may have a shaft 234, a head 236, and a neck 248 connecting the shaft 234 and the head 236. The shaft 234 and neck 248 may be of the type described above with reference to shaft 134 and neck 148 as described above and which will not be described again here for brevity sake. The head 236 may include a first arm 238, a second arm 240, and a passageway 242 extending between the first arm 238 and the second arm 240. The first arm 238 and second arm 240 each have an interior surface formed by the passageway 242. The passageway 242 also forms a base 246 near the bottom of the bottom of the head 226 which couples to the shaft 234. The first arm 238 and second arm 240 may, for example, each include an opening 244 extending from the interior surface to an exterior surface of the arms 238, 240. The opening 244 may be a tapered opening which, for example, is larger near the top of the head 236 and tapers as the opening 244 extends toward the shaft 234. The at least one hinge member 258 may be positioned within the opening 244 in the first arm 238 and the second arm 240. In addition, the hinge member 258 may also, for example, pass through the elongate member 250 to secure the elongate member 250 to the second fastener 232.

Figure 8:
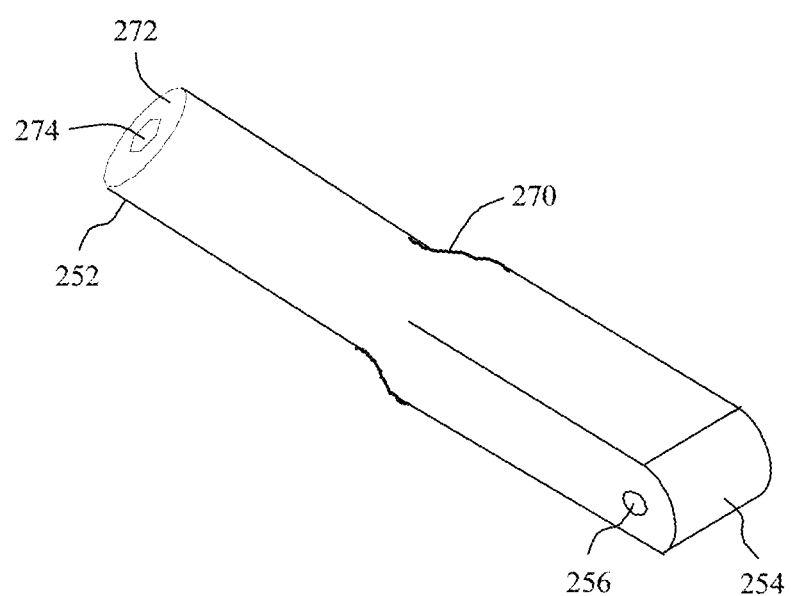
FIG. 8 is a perspective view of an alternative elongate member for the single level fusion system of FIG. 1 or FIG. 6, in accordance with an aspect of the present invention.

The elongate member 250, as shown in FIGS. 6 and 8, includes a first end 252 and a second end 254. The elongate member 250 may be round at the first end 252 and rectangular at the second end 254. The elongate member 250 may include an opening 256 near the second end 254 to receive the at least one hinge member 258. The elongate member 250 may have a tapered portion 270 positioned between the round first end 252 and the rectangular second end 254. The elongate member 250 may also have an end surface 272 with an opening 274.

The system 200 may be implanted by first obtaining a first fastener assembly 210, a second fastener assembly 230, and an elongate member 250. Then the elongate member 250 may be coupled to the second fastener assembly 230 by inserting the hinge member 258 into the openings 244 in the second fastener 232 to secure the elongate member 250 to the second fastener 232. Next, the first fastener 212 and the second fastener assembly 230 with the attached elongate member 250 may each be inserted into the desired vertebrae. After insertion of the first fastener 212 and the second fastener 232, the elongate member 250 may be moved into position between the first arm 218 and second arm 220 of the first fastener 212. Next, a first set screw 260 may be inserted at least partially to secure the elongate member 250 into the head 236 of the first fastener 212. The first set screw 260 may be inserted partially to allow for the surgeon to slide the elongate member 250 within the passageway 222 to position the first fastener 212 with respect to the second fastener 232 to maintain or re-establish proper spacing and alignment within the patient's spine. The second end 254 of the rod 250 may also be slid within the opening 244 to the desired position. Once the desired position is achieved, the first set screw 260 may be tightened to secure the elongate member 250 at the first end 252 and a second set screw 260 may be inserted into the head 236 of the second fastener 232 and tightened to secure the elongate member 250 at the second end 254.

Figure 7:
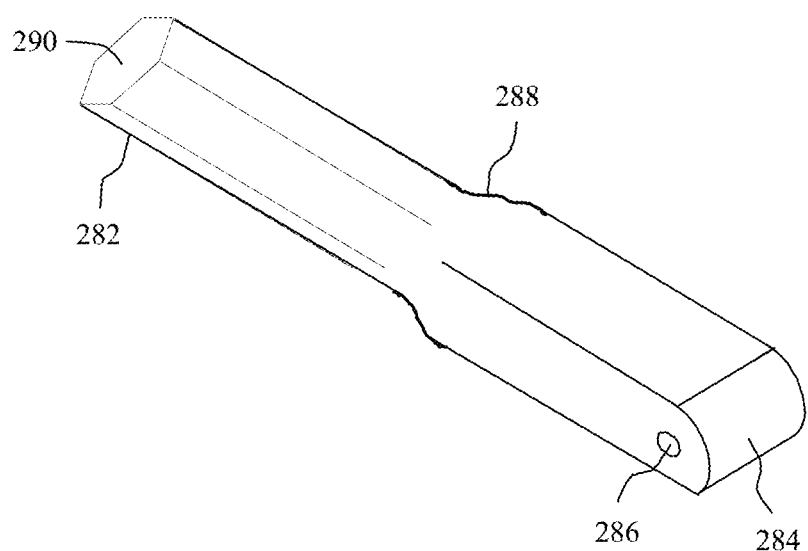
FIG. 7 is a perspective view of an alternative elongate member for the single level fusion system of FIG. 1 or FIG. 6, in accordance with an aspect of the present invention.

An alternative elongate member 280 is shown in FIG. 7. The elongate member 280 includes a first end 282 and a second end 284. The first end 282 of the elongate member 280 may have a polygon shape, such as a hexagon shape, and the second end 284 may have a rectangular shape. The elongate member 280 may include an opening 286 near the second end 284 to receive the at least one hinge member 258. The elongate member 280 may have a tapered portion 288 positioned between the polygonal first end 282 and the rectangular second end 284. The elongate member 280 may also have an end surface 290. It is also contemplated that the elongate members disclosed herein may have multiple shapes including but not limited to square, rectangle, round, hexagonal, as well as any combination of these shapes depending on the fasteners that the elongate members are engaging.

Figure 9:
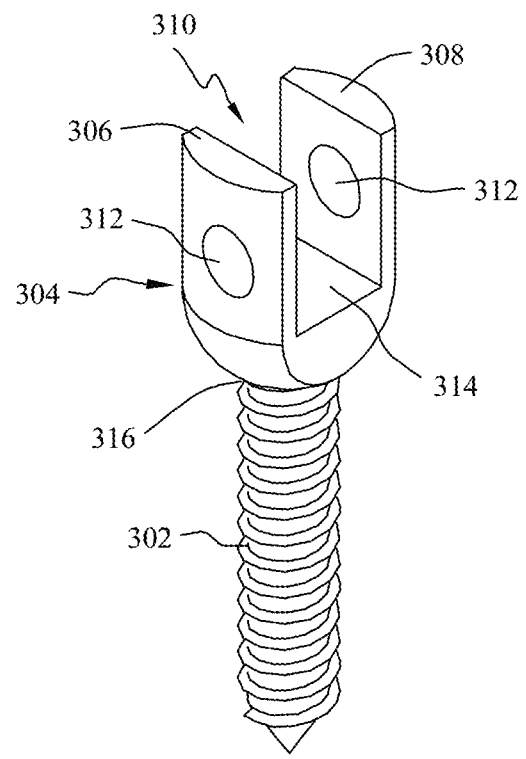
FIG. 9 is a perspective view of a fastener for a single level fusion system such as that of FIG. 1 or FIG. 6, in accordance with an aspect of the present invention.

A fastener member 300 is shown in FIG. 9. The fastener member 300 includes a shaft 302, a head 304, and a neck portion 316 connecting the shaft 302 and the head 304. The head 304 may include a first arm 306, a second arm 308, and a passageway 310 extending between the first arm 306 and second arm 308. The first arm 306 and second arm 308 each have an interior surface formed by the passageway 310. The passageway 310 also forms a base 314 near the bottom of the head 304. The base 314 may be, for example, planar or curved to correspond to the elongate member being received within the head 304 of the fastener member 300. The first arm 306 and the second arm 308 may each have, for example, openings 312 extending from the interior surface to an exterior surface of the arms 306, 308. The openings 312 may be configured to receive, for example, a larger hinge member to provide for a stronger connection between the fastener member 300 and an elongate rod. The shaft 302 may be, for example, threaded along its entire length, threaded along only a portion of the its length, or non-threaded.

Figure 10:
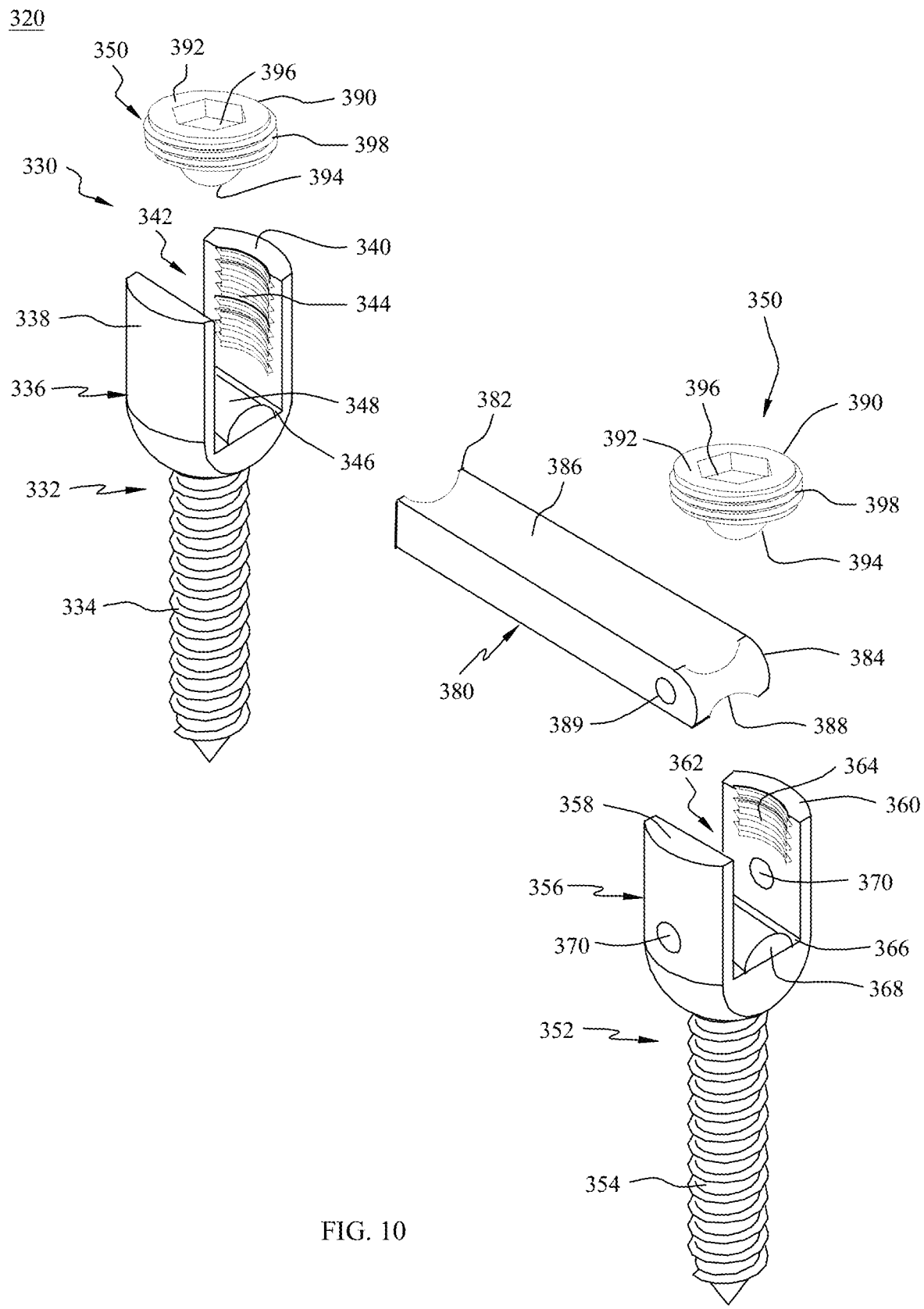
FIG. 10 is an exploded perspective view of another embodiment of a single level fusion system, in accordance with an aspect of the present invention.

Referring now to FIG. 10, an alternative embodiment of a single level fusion system 320 is shown. The system 320 may include a first fastener assembly 330, a second fastener assembly 350, and an elongate member 380. The first fastener assembly 330 may include a first fastener 332 and a set screw 390. The first fastener 332 may include a shaft 334 and a head 336 coupled to the top of the shaft 334. The shaft 334 may be of the type described above with reference to shaft 114. The head 336 may include a first arm 338, a second arm 340, and passageway 342 extending between the first arm 338 and the second arm 340. The first arm 338 and second arm 340 each have an interior surface formed by the passageway 342. The passageway 342 also forms a base 346 near the bottom of the head 336. The first arm 338 and the second arm 340 may have, for example, a threaded portion 344 that extends along at least a portion of the interior surface of the first arm 338 and the second arm 340 from the top surface of the first and second arms 338, 340 toward the base 346. The base 346 may include, for example, a protrusion 348 extending out from the base 346. The protrusion 348 may alternatively be a ball or sphere to allow for the elongate member 380 to pivot with respect to the first fastener 332. A ball or sphere protrusion 348 provides a bi-radius feature that allows for angulation of the rod in the sagittal plane.

As shown in FIG. 10, the second fastener assembly 350 may include a second fastener 352 and a set screw 390. The second fastener 352 may be of the type described above with reference to first fastener 332. The shaft 354, first arm 358, second arm 360, passageway 362, base 366, and protrusion 368 may be of the type described above with reference to shaft 334, first arm 338, second arm 340, passageway 342, base 346, and protrusion 348, as described above and which will not be described again here for brevity sake. The second fastener 352 may further include openings 370 extending from the exterior surface to an interior surface.

With continued reference to FIG. 10, the set screws 390 may include a top surface 392, a bottom surface 394, and threads 398 positioned on the exterior surface of the set screws 392 and extending from the top surface 392 to the bottom surface 394. The set screw 390 may also include a tool engagement opening 396 extending into the set screws 390 from the top surface 392 toward the bottom surface 394. In addition, the bottom surface 394 of the set screws 390 may include a protrusion extending away from the set screw 390.

The elongate member 380, as shown in FIG. 10, may include a first end 382 and a second end 384. The elongate member 380 may include a first recess 386 extending from a top surface of the elongate member 380 toward the bottom surface and between the first end 382 and the second end 384. In addition, the elongate member 380 may also include a second recess 388 extending from a bottom surface of the elongate member 380 toward the top surface and between the first end 382 and the second end 384. The first recess 386 and second recess 388 of the elongate member 380 are sized and shaped to correspond to the protrusions 348, 368. When the elongate member 380 is positioned within the heads 336, 356, the recesses 386, 388 mate with the protrusions 348, 368. In addition, the protrusions on the bottom surface 394 of the set screws 390 are sized and shaped to engage the recess 386 to allow the set screws 390 to securely couple the elongate member 380 to the first and second fasteners 332, 352.

A method for inserting the devices 100, 200, and 320 of FIGS. 1-6 and 10 into a patient may include cutting a small incision in the patient, for example, a 3 cm incision. Next the fascia is cut and muscles are split in line of the fibers to expose the patient's vertebrae. Once the vertebrae are exposed, an image guidance or fluoroscopy device may be used to insert a first fastener or pedicle screw 110, 210, 330 into a first pedicle of a first vertebra. Then, the second fastener or pedicle screw 130, 230, 350 with the elongate member 150, 250, 380 is coupled to and in line with the longitudinal axis of the second fastener 130, 230, 350 may be inserted into an adjacent pedicle of a second vertebra. The fasteners 110, 210, 330, 130, 230, 350 may be inserted using a guide wire or free hand. Next, the elongate member 150, 250, 380 is turned perpendicular to the fasteners 110, 210, 330, 130, 230, 350 and inserted in the desired position in the head 116, 216, 336 of the first fastener 110, 210, 330. A locking mechanism, for example, set screws 160, 260, 350 may be inserted into the head 116, 216, 336 of the first fastener 110, 210, 330 and tightened down to secure the elongate member 150, 250, 380 to the first fastener 110, 210, 330. A second locking mechanism, for example, set screws 160, 260, 350, may also optionally be inserted into the head 136, 236, 356 of the second fastener 130, 230, 350. Finally, the patient's incision may be closed.

Figure 11:
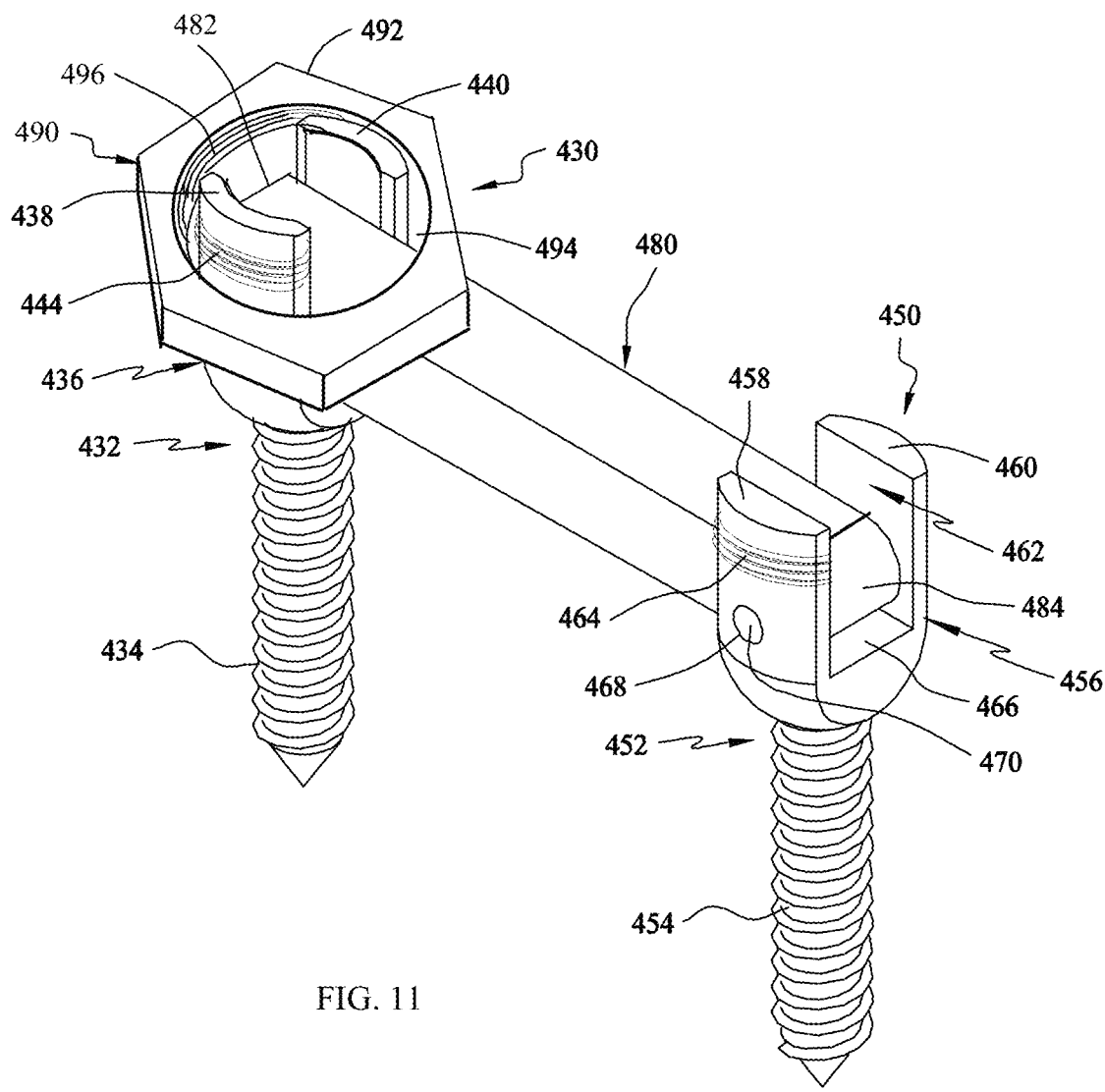
FIG. 11 is a perspective view of another embodiment of a single level fusion system, in accordance with an aspect of the present invention.

Another single level fusion system 420 is depicted in FIG. 11. The single level fusion system 420 may include a first fastener assembly 430, a second fastener assembly 450, and an elongated member 480. The first fastener assembly 430 may include a first fastener 432 and a fastener 490. The first fastener 432 may be of the type described above with reference to first fastener 112, which will not be described again here for brevity sake. The first fastener 432 may also include a threaded portion 444 on the exterior of head 436.

As shown in FIG. 11, the fastener 490 may include an exterior surface 492 and an interior surface 494. The interior surface 494 may be threaded to secure the fastener 490 to the head 436 of the first fastener 432. As seen in FIG. 11, the fastener 490 may have a shape of, for example, a polygon, such as a hexagon.

The second fastener assembly 450, as shown in FIG. 11, may include a second fastener 452 and a hinge member 470. The second fastener 452 may be of the type described above with reference to second fastener 132, which will not be described again here for brevity sake. The second fastener 452 may also include a threaded portion 464 on the exterior of head 456. The at least one hinge member 470 may be positioned within the openings 468 in the first and second arms 458, 460. The at least one hinge member 470 may also, for example, pass through the elongate member 480 to secure the elongate member 480 to the second fastener 452.

A method for inserting the single level fusion system 420 of FIG. 11 into a patient may include cutting a small incision in the patient, for example, a 3 cm incision. Next the fascia is cut and muscles are split in line of the fibers to expose the patient's vertebrae. Once the vertebrae are exposed, an image guidance or fluoroscopy device may be used to insert a first fastener or pedicle screw 430 into a first pedicle of a first vertebra. Then the second fastener or pedicle screw 450 with the elongate member 480 coupled to and extended in line with the longitudinal axis of the second fastener 450 may be inserted into an adjacent pedicle of a second vertebra. The fasteners 430, 450 may be inserted using a guide wire or free hand. Next the elongate member 480 is turned perpendicular to the fasteners 430, 450 and inserted in the desired position in the head 436 of the first fastener 430. A locking mechanism, for example, a nut 490 is then secured around the head 436 of the first fastener 430 and tightened down to secure the elongate member 480 to the first fastener 430. A second locking mechanism, for example, a nut or set screw (not shown), may also optionally be secured to the head 456 of the second fastener 450 to secure the elongate member 480 to the second fastener 450. Finally, the patient's incision may be closed The fasteners 112, 132, 212, 232, 332, 352, 432, and 452 may be cannulated through the center of the shaft along the long axis of the fasteners 112, 132, 212, 232, 332, 352, 432, and 452 and include an opening (not shown) to enable insertion over a guide wire, k-wire, pin, or the like to assist with insertion into the patient.

The elongate members 150, 250, 280, 290, 380, 480, 550, and 650 may have a length. The length of the elongate members 150, 250, 280, 290, 380, 480, 550, and 650 will be selected based on the procedure being performed and whether compression or distraction is desired. For example, a rod that is longer than the position of the in situ fasteners will be used for distraction to move the engaged vertebrae apart and a rod that is shorter than the in situ position of the fasteners will be used for compression to pull the engaged vertebrae together. The length of elongate members 150, 250, 280, 290, 380, 480, 550, and 650 may range from, for example, approximately 10 mm to 60 mm and more specifically approximately 20 mm to 50 mm. The elongate members 150, 250, 280, 290, 380, 480, 550, and 650 may be straight or curved along the longitudinal axis.

Figure 12:
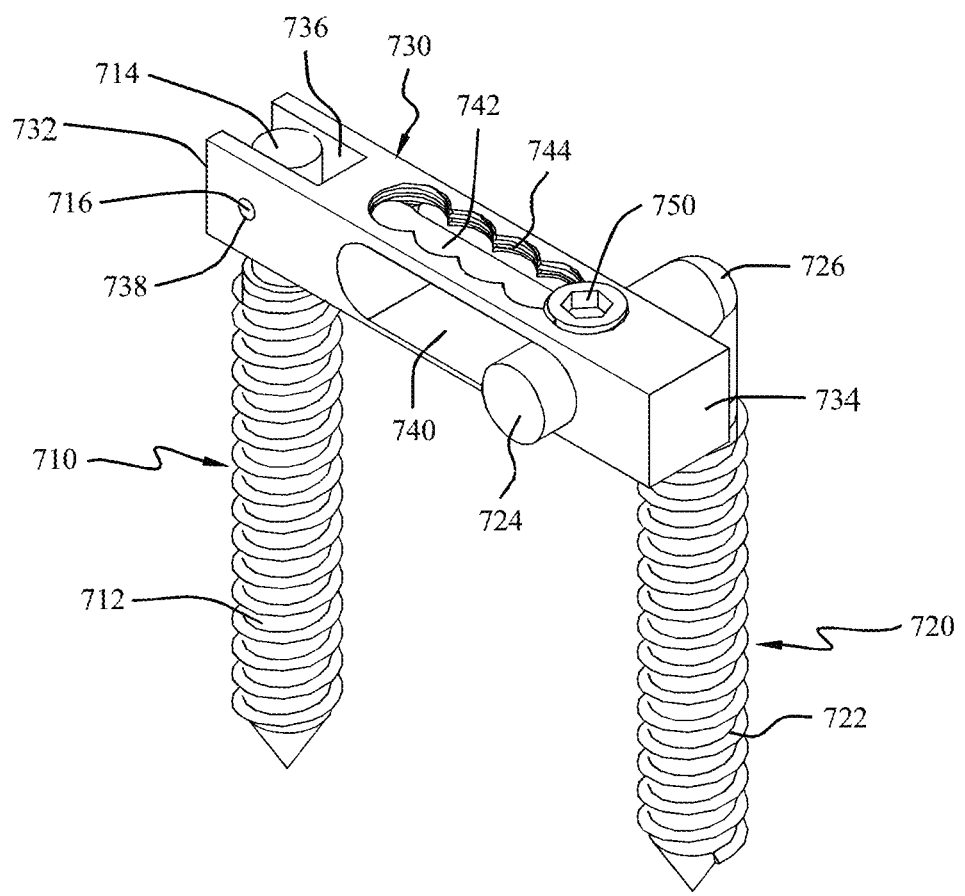
FIG. 12 is a perspective view of yet another embodiment of a single level fusion system, in accordance with an aspect of the present invention.
Figure 13:
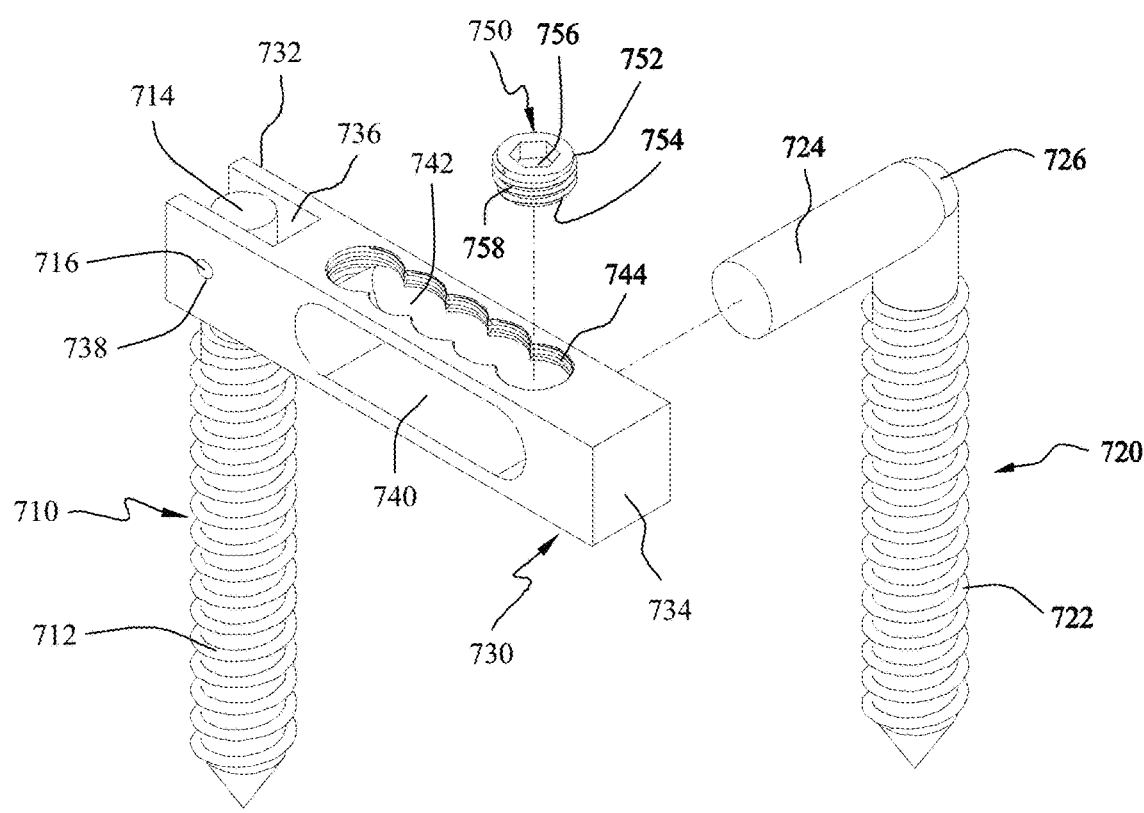
FIG. 13 is a partially exploded perspective view of the single level fusion system of FIG. 12, in accordance with an aspect of the present invention.
Figure 14:
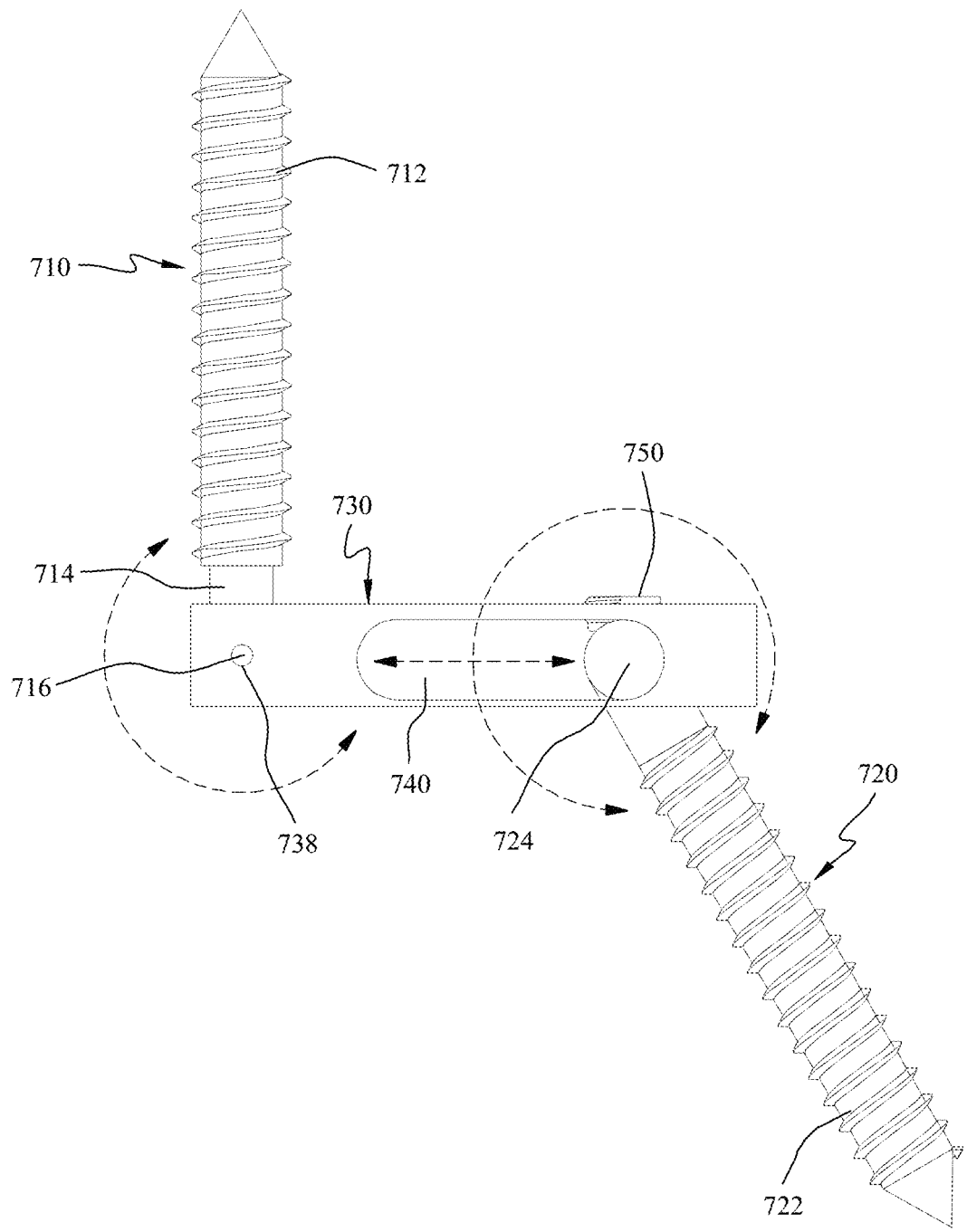
FIG. 14 is a side view of the single level fusion system of FIG. 13, in accordance with an aspect of the present invention.
Figure 15:
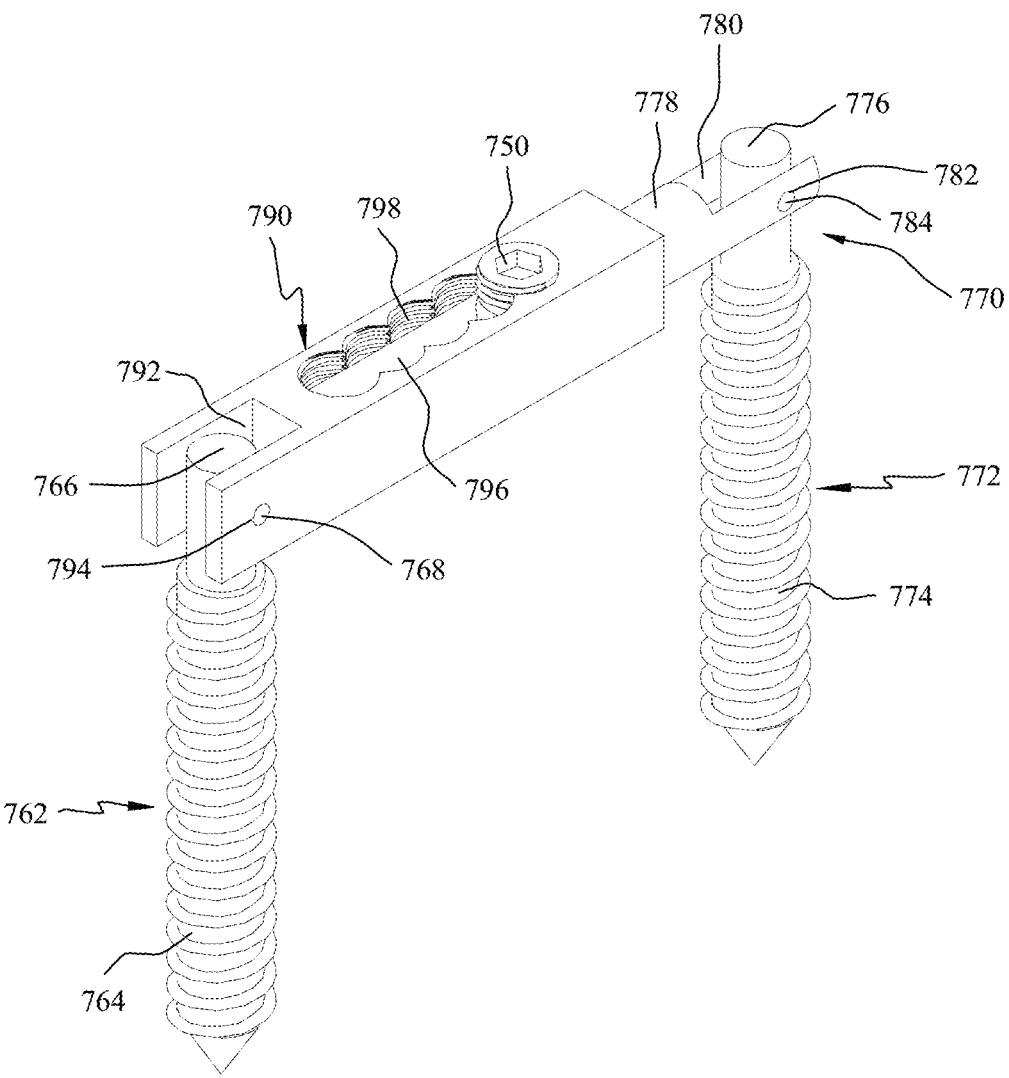
FIG. 15 is a perspective view of another single level fusion system, in accordance with an aspect of the present invention.
Figure 16:
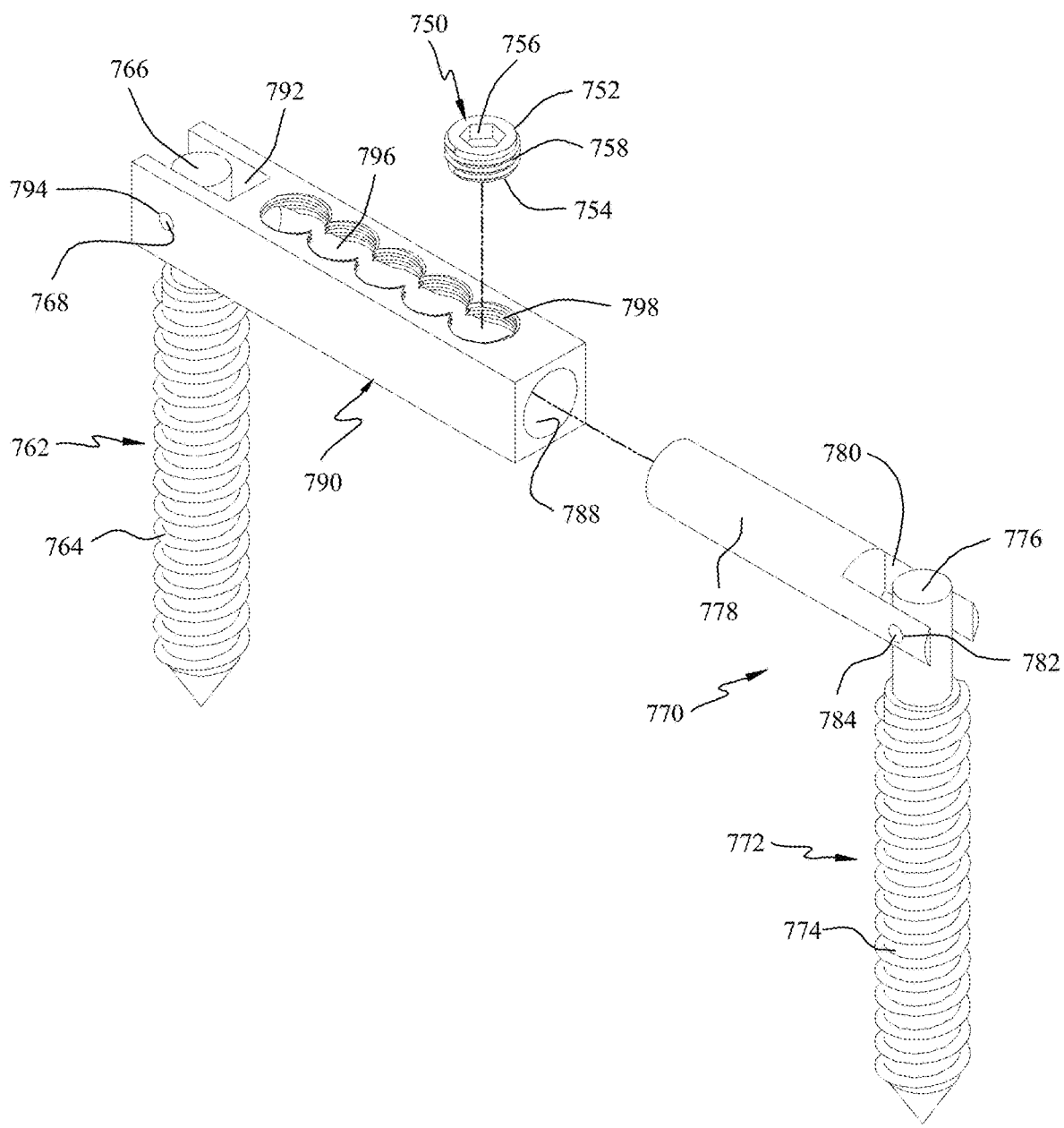
FIG. 16 is a partially exploded perspective view of the single level fusion system of FIG. 15, in accordance with an aspect of the present invention.

Referring now to FIGS. 12-14, a single level fusion system 700 is shown. The single level fusion system 700 may include a first fastener 710, a second fastener 720, an elongate member 730, and a set screw 750. The first fastener 710 may include a shaft 712 and an attachment portion 714 with an opening (not shown). The shaft 712 may be, for example, threaded from the attachment portion 714 to the tip or along only a portion of the length from the attachment portion 714 to the tip.

The second fastener 720, as shown in FIGS. 12-14, may include a shaft 722, an attachment portion 724, and a connector portion 726 that couples the shaft 722 to the attachment portion 724 at approximately a 90° angle. The shaft 722 may be, for example, threaded from the connector portion 726 to the tip or along only a portion of the length from the connector portion 726 to the tip. The attachment portion 724 and connector portion 726 may be round.

The elongate member 730 may have a first end 732 and a second end 734, as shown in FIGS. 12-14. The elongate member 730 may also include an attachment groove 736 in the first end 732. The first end 732 may also include at least one opening 738 extending from the exterior surface of the elongate member 730 into the attachment groove 736. The elongate member 730 may also have a first opening 740 extending through the elongate member 730 from a first side to a second side for receiving the attachment portion 724 of the second fastener 720. The first opening 740 may have, for example, an oval shape. In addition, the elongate member 730 may include a second opening 742 extending from a top surface into the first opening 740. The second opening 742 may include, for example, a plurality of overlapping screw holes forming a scalloped shaped second opening 742. The second opening 742 may include threads 744.

The single level fusion system 700 may also include a set screw 750. As seen in FIG. 13, the set screw 750 may include a top surface 752 and a bottom surface 754. The set screw 750 may also include a tool engagement opening 756 extending into the set screw 750 from the top surface 752 toward the bottom surface 754. In addition, the set screw 750 may include threads 758 on the exterior surface extending from the top surface 752 to the bottom surface 754.

With continued reference to FIGS. 12-14, the single level fusion system 700 may be assembled by inserting the attachment portion 714 of the first fastener 710 into the attachment groove 736 of the elongate member 730 and aligning the opening (not shown) in the attachment portion 714 with the openings 738 in the elongate member 730. Next, a hinge member 716 may be inserted through an opening 738 in the elongate member 730 and the opening (not shown) in the attachment portion 714 to moveably couple the first fastener 710 to the elongate member 730. In use, the first fastener 710 and coupled elongate member 730 may be inserted into a first vertebra in a patient and the second fastener 720 may be inserted into a second adjacent vertebra. Then, the attachment portion 724 may be inserted into the first opening 740. The attachment portion 724 may be translated within the first opening 740 until a desired position is achieved, then the set screw 750 may be inserted into the second opening 742 to secure the attachment portion 724 to the elongate member 730. When the set screw 750 is inserted into the second opening 742, the threads 758 of the set screw 750 engage one set of threads 744 in the second opening 742.

The fasteners 710, 720 and the elongate member 730 may be cannulated through the center of the shafts along a longitudinal axis to enable insertion over a guide wire, k-wire, pin, or the like to assist with insertion into the patient.

A method for inserting the single level fusion system 700 of FIGS. 12-14 into a patient may include cutting a small incision in the patient, for example, a 3 cm incision. Next the fascia is cut and muscles are split in line of the fibers to expose the patient's vertebrae. Once the vertebrae are exposed, an image guidance or fluoroscopy device may be used to insert a first fastener or pedicle screw 710 with the elongate member 730 extended in line with the longitudinal axis of the fastener 710 into a first pedicle of a first vertebra. A second fastener or pedicle screw 720 may then be inserted into an adjacent second pedicle of a second vertebra. The fasteners 710, 720 may be inserted using a guide wire if the fasteners 710, 720 are cannulated or free hand. Then the elongate member 730 may be turned perpendicular to the fastener 710. Next the attachment portion 724 of the second fastener 720 may be turned into the slot 740 of the elongate member 730. A locking mechanism, for example, a set screw 750 may be inserted into a desired position in the second opening 742 of the elongate member 730 and tightened down to secure the second fastener 720 to the elongate members 730. Finally, the patient's incision may be closed.

Another single level fusion system 760 is shown in FIGS. 15-19 and includes a first fastener 762, a second fastener assembly 770, and an elongate member 790. The first fastener 762 may include a shaft 764 and an attachment portion 766 with an opening (not shown). The shaft 764 may be, for example, threaded from the attachment portion 766 to the tip or along only a portion of the length from the attachment portion 766 to the tip.

The second fastener assembly 770, as shown in FIGS. 15-19, includes a second fastener 772 and a translating rod 778. The second fastener 772 may include a shaft 774 and an attachment portion 776 with an opening (not shown). The shaft 774 may be, for example, threaded from the attachment portion 776 to the tip or along only a portion of the length from the attachment portion 776 to the tip. The translating rod 778 may include an attachment groove 780 in the second end of the translating rod 778. The second end may also include at least one opening 782 extending from the exterior surface of the translating rod 778 into the attachment groove 780. The second fastener 772 may be attached to the translating rod 778 by aligning the opening (not shown) in the second fastener 772 with the at least one opening 782 in the translating rod 778. Then, a hinge member 784 may be inserted and secured to couple the second fastener 772 to the translating rod 778.

The elongate member 790 may have a first end and a second end, as shown in FIGS. 15-19. The elongate member 790 may also include an attachment groove 792 in the first end. The second end may include a first opening 788 extending from the second end of the elongate member 790 toward the first end through the interior of the elongate member 790. The first opening 788 may be sized to receive the translating rod 778 of the second fastener assembly 770. The first opening 740 may have, for example, a round shape or other shape to match the shape of the translating rod 778. In addition, the elongate member 790 may include a second opening 796 extending from a top surface into the first opening 788. The second opening 796 may include, for example, a plurality of overlapping screw holes forming a scalloped shaped second opening 796. The second opening 796 may include threads 798 in each of the overlapping screw holes.

With continued reference to FIGS. 15-19, the single level fusion system 760 may be assembled by inserting the attachment portion 766 of the first fastener 762 into the attachment groove 792 of the elongate member 790 and aligning the opening (not shown) in the attachment portion 766 with the openings 794 in the elongate member 790. Next, a hinge member 768 may be inserted through the opening 794 in the elongate member 790 and the opening (not shown) in the attachment portion 766 to moveably couple the first fastener 762 to the elongate member 790. The second fastener 772 may be coupled to the translating rod 778 to form the second fastener assembly 770. The second fastener 772 may be coupled to the translating rod 778 by aligning the opening (not shown) in the attachment portion 776 of the second fastener 772 with the at least one opening 782 in the elongate member 790. In use, the first fastener 762 and coupled elongate member 790 may be inserted into a first vertebra in a patient and the second fastener assembly 770 may be inserted into a second adjacent vertebra. Then the translating rod 778 may be inserted into the first opening 788. The translating rod 778 may be slid within the first opening 788 until a desired position is achieved. Then, the set screw 750 may be inserted into the second opening 796 to secure the translating rod 778 of the second fastener assembly 770 to the elongate member 790. When the set screw 750 is inserted into the second opening 796, the threads 758 of the set screw 750 engage one set of threads 798 in the second opening 796.

Figure 17:
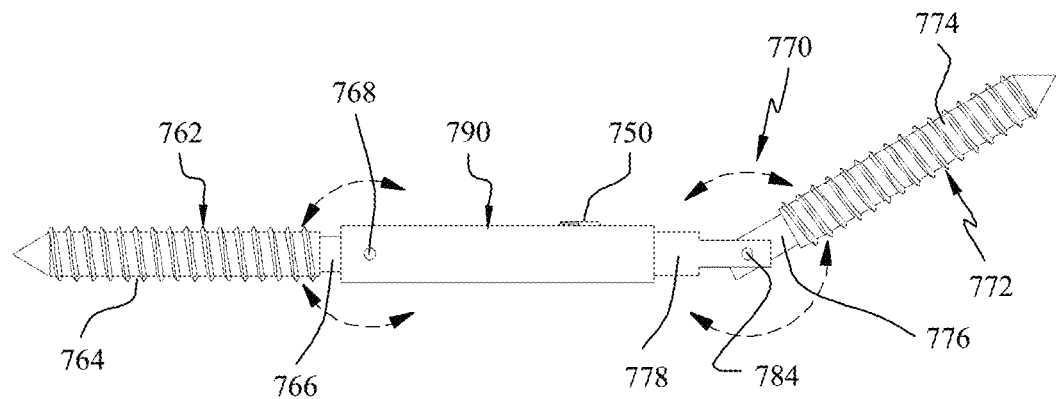
FIG. 17 is a first side view of the single level fusion system of FIG. 15, in accordance with an aspect of the present invention.
Figure 18:
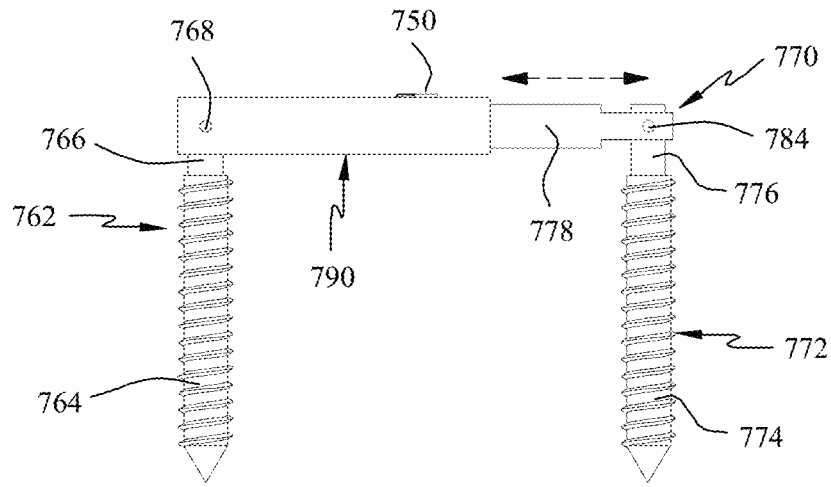
FIG. 18 is a second side view of the single level fusion system of FIG. 15, in accordance with an aspect of the present invention.
Figure 19:
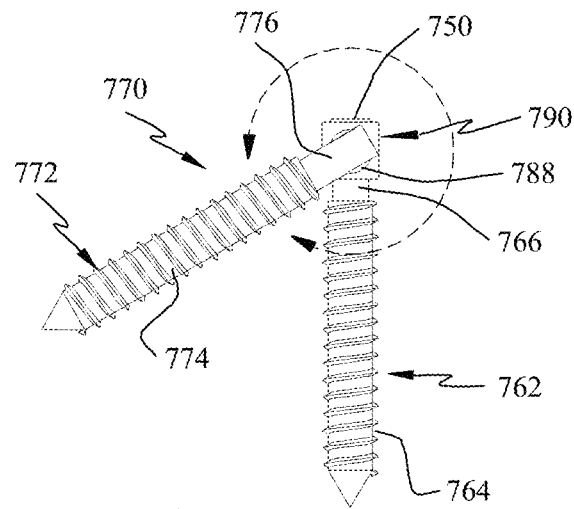
FIG. 19 is an end view of the single level fusion system of FIG. 15, in accordance with an aspect of the present invention.

As illustrated in FIG. 17, the first fastener 762 may rotate with respect to the elongate member 790, for example, almost 360° being restrained only by contact with the elongate member 790. The second fastener 772 may also rotate with respect to the translating rod 778, for almost 360° and again only be restrained by contact with the translating rod 778. The fasteners 762, 772 each have a variable range of motion and the angle of the fasteners 762, 772 after implantation will generally be determined by the patient's anatomy. In addition, as shown in FIG. 18, the second fastener assembly 770 may translate into and out of the elongate member 790. Further, as shown in FIG. 19, the second fastener assembly 770 may rotate approximately 360° within the opening 788 of the elongate member 790.

The fasteners 762, 772, translating rod 778, and the elongate member 790 may be cannulated through the center of the shafts along a longitudinal axis to enable insertion over a guide wire, k-wire, pin, or the like to assist with insertion into the patient.

A method for inserting the single level fusion system 760 of FIGS. 15-19 into a patient may include cutting a small incision in the patient, for example, a 3 cm incision. Next the fascia is cut and muscles are split in line of the fibers to expose the patient's vertebrae. Once the vertebrae are exposed, an image guidance or fluoroscopy device may be used to insert a first fastener or pedicle screw 762 with the coupled elongate member 790 extended in line with the longitudinal axis of the fastener 762 into a first pedicle of a first vertebra. A second fastener or pedicle screw 772 with the coupled translating rod 778 extended in line with the longitudinal axis of the fastener 772 may then be inserted into an adjacent second pedicle of a second vertebra. The fasteners 762, 772 may be inserted using a guide wire if the fasteners 762, 772, translating rod 778, and elongate member 790 are cannulated or free hand. Then the elongate member 790 may be turned perpendicular to the fastener 762 and the translating rod 778 may be turned perpendicular to the fastener 772. Next, the translating rod 778 may be inserted into the first opening 788 of the elongate member 790. A locking mechanism, for example, a set screw 750 may be inserted into a desired position in the second opening 796 of the elongate member 790 and tightened down to secure the translating rod 778 of the second fastener assembly 770 to the elongate member 790. Finally, the patient's incision may be closed.

Figure 20:
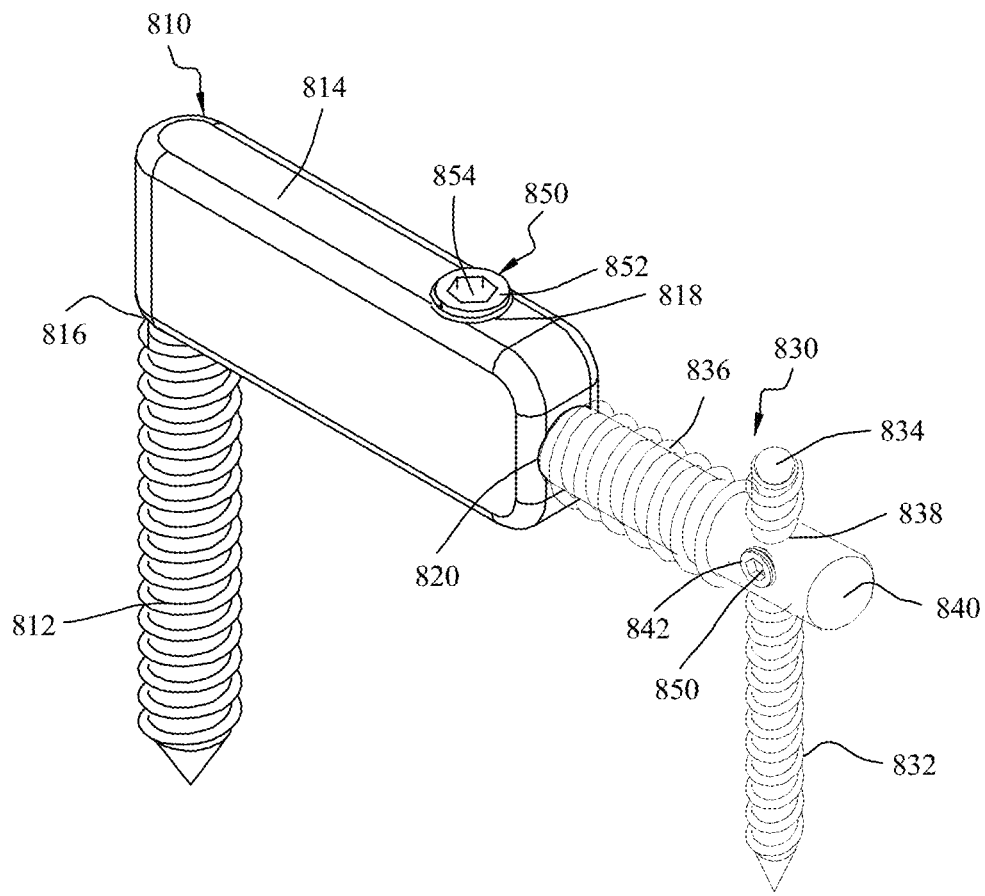
FIG. 20 is a perspective view of another single level fusion system, in accordance with an aspect of the present invention.
Figure 21:
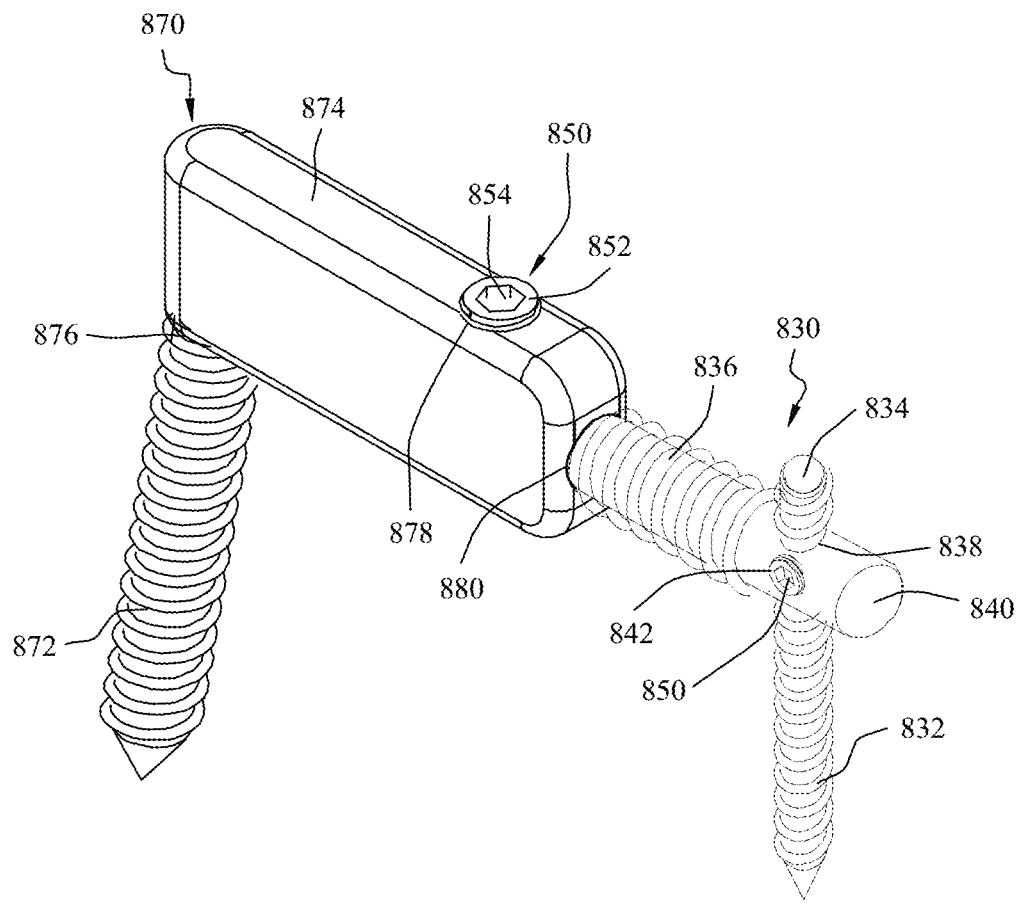
FIG. 21 is a perspective view of yet another single level fusion system, in accordance with an aspect of the present invention.

FIGS. 20-21 show single level fusion systems 800, 860. The single level fusion system 800, as shown in FIG. 20, may include a first fastener assembly 810 and a second fastener assembly 830. The first fastener assembly 810 may include a shaft 812, an elongate member 814, and a neck 816 for securing the shaft 812 to the elongate member 814. The shaft 812 may, for example, be attached perpendicular to the elongate member 814 and the shaft 812 may be fixed or rotatable with respect to the elongate member 814. The elongate member 814 may include a body with the shaft 812 attached at a first end and a first opening 820 at the second end for receiving the second fastener assembly 830. The first opening 820 may extend from the second end into the body of the elongate member 814 toward the first end. The elongate member 814 may also include a second opening 818 extending from the top surface into the first opening 820. The opening 820 may be, for example, threaded. The second fastener assembly 830 may include a second fastener 832 and a threaded rod 836. The threaded rod 836 may include a non-threaded portion 840 at a second end. The portion 840 may include a first opening 838 extending entirely through the threaded rod 836 perpendicular to the longitudinal axis of the threaded rod 836. The threaded rod 836 may also include a second opening 842 extending from a side of the threaded rod 836 through to the first opening 838. The first opening 838 and second opening 842 may be positioned relatively perpendicular. The second opening 842 may be configured to receive a locking mechanism 850. The second opening 842 may be, for example, threaded to receive the locking mechanism 850. The second fastener 832 may have a first end 834 and a second end which may be pointed. The second fastener 832 may be attached to the threaded rod 836 by inserting the first end 834 of the second fastener 832 into the opening 838 in the threaded rod 836. Once the second fastener 832 is in a desired position with respect to the threaded rod 836, then a locking mechanism 850 may be inserted to secure the second fastener 832 to the threaded rod 836. The single level fusion system 800 may be formed by screwing the threaded rod 836 of the second fastener assembly 830 into the opening 820 in the elongate member 814 of the first fastener assembly 810.

The single level fusion system 860, as shown in FIG. 21, may include a first fastener 870 and a second fastener assembly 830. The first fastener assembly 870 may include a shaft 872, an elongate member 874, and a neck 876 for securing the shaft 872 to the elongate member 874. The shaft 872 may be, for example, attached angled to the elongate member 874 and the shaft 872 may be fixed or rotatable with respect to the elongate member 874. The elongate member 874 may include a body with the shaft 872 attached at a first end and a first opening 880 at the second end for receiving the second fastener assembly 830. The first opening 880 may extend from the second end into the body of the elongate member 874 toward the first end. The first opening 880 may be, for example, threaded. The elongate member 874 may also include a second opening 878 extending from the top surface into the first opening 880. The second fastener assembly 830 is of the type described above with reference to FIG. 20. The single level fusion system 860 may be formed by screwing the threaded rod 836 of the second fastener assembly 830 into the opening 880 in the elongate member 874 of the first fastener assembly 870.

The locking mechanisms 850 may be, for example, set screws of the type described above with reference to set screw 750, which will not be described again here for brevity sake. Alternative locking mechanisms 850 are also contemplated to secure the portions of the single level fusion systems 800, 860 together. The set screws 850, as shown in FIGS. 20-21, include a top surface 852 and a tool engagement opening 854.

The shaft 812 and fastener 832 and the elongate member 730 may be cannulated through the center of the shafts along a longitudinal axis to enable insertion over a guide wire, k-wire, pin, or the like to assist with insertion into the patient.

A method for inserting the single level fusion systems 800, 860 of FIGS. 20-21 into a patient may include cutting a small incision in the patient, for example, a 3 cm incision. Next the fascia is cut and muscles are split in line of the fibers to expose the patient's vertebrae. Once the vertebrae are exposed, an image guidance or fluoroscopy device may be used to insert the first fastener 810, 870 with the elongate member 814, 874 extended in line with the longitudinal axis of the fastener 810, 870 into a first pedicle of a first vertebra.

Then the threaded rod 836 may be inserted or screwed into the first opening 820, 880 of the elongate member 814, 874. The threaded rod 836 may be screwed to a desired position with respect to the elongate member 814, 874 and the length of the threaded rod 836 extending out from the elongate member 814, 874 will determine the amount of compression or distraction of the two vertebrae. Next the second fastener 832 is inserted through the first opening 838 on the distal end of the threaded rod 836 and into a second pedicle in a second adjacent vertebra. The fasteners 762, 772 may be inserted using a guide wire if the fasteners are cannulated or free hand. The second fastener 832 may be secured to the threaded rod 836 by inserting a locking mechanism, for example, a set screw 850 into the second opening 842 in the threaded rod 836. Then a locking mechanism, for example, a cap or set screw 850, may be inserted into the second opening 818, 878 and tightened down to secure the threaded rod 836 to the elongate member 814, 874. Finally, the patient's incision may be closed.

Figure 22:
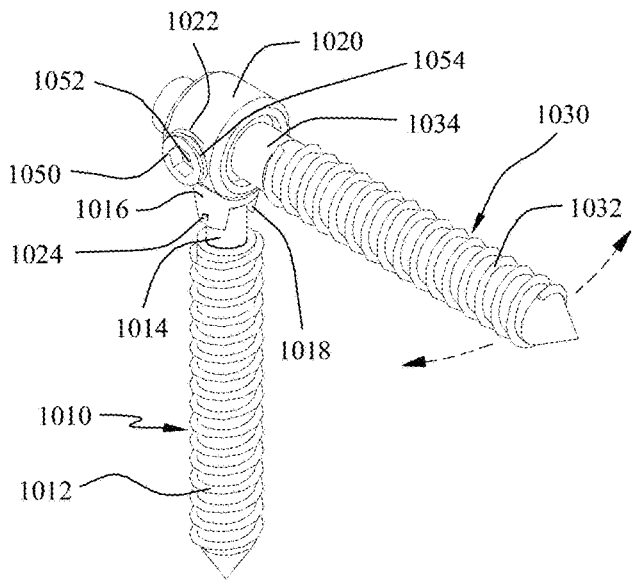
FIG. 22 is a perspective view of another single level fusion system, in accordance with an aspect of the present invention.
Figure 23:
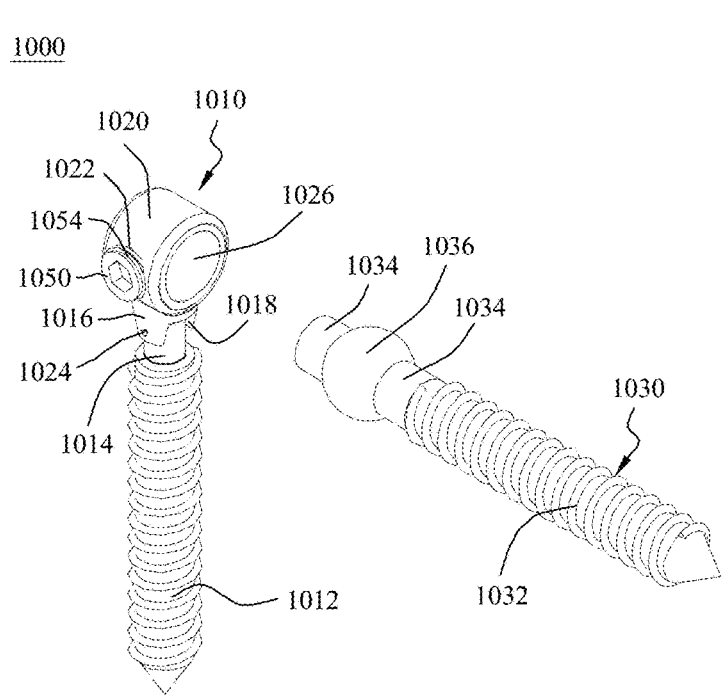
FIG. 23 is an exploded perspective view of the single level fusion system of FIG. 22, in accordance with an aspect of the present invention.
Figure 24:
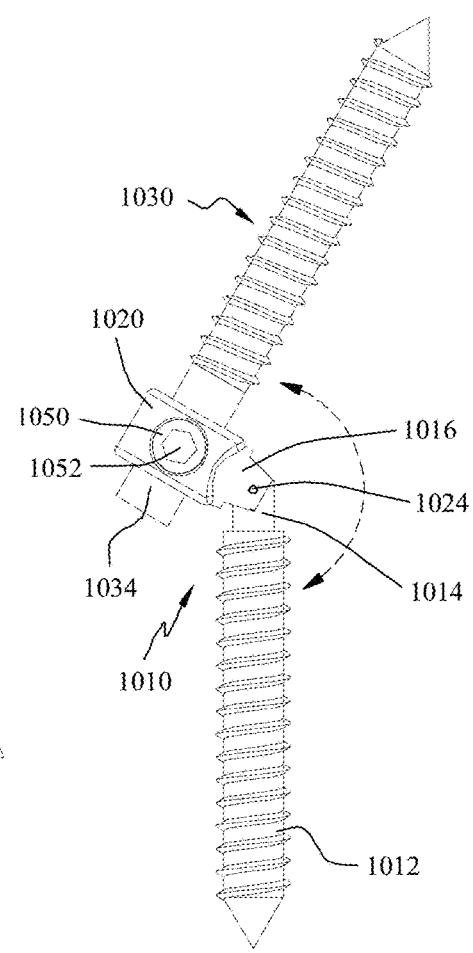
FIG. 24 is a side view of the single level fusion system of FIG. 22, in accordance with an aspect of the present invention.

A single level fusion device 1000 is shown in FIGS. 22-24. The single level fusion device 1000 may include a first fastener 1010 and a second fastener 1030. The first fastener 1010 may include a shaft 1012, a head 1020, and a neck 1016 extending out of the head 1020 for coupling the shaft 1012 to the head 1020. The shaft 1012 may include a threaded portion and an attachment portion 1014. The head 1020 may include a first opening 1022 and a second opening 1026. The first opening 1022 may extend through the head 1020 and into the second opening 1026. The first opening 1022 may be threaded to receive a set screw 1050. The neck 1016 may include two arms 1018. The neck 1016 may also include an opening (not shown) to receive a hinge member 1024. The attachment portion 1014 of the shaft 1012 may be positioned between the two arms 1018 of the neck 1016 aligning an opening (not shown) in the attachment portion 1014 with the opening (not shown) in the neck 1016 and the hinge member 1024 inserted into the openings to moveably couple the head 1020 to the shaft 1012. The hinge member 1024 allows for the head 1020 to pivot or rotate relative to the shaft 1012. The second fastener 1030, as shown in FIGS. 22-24, may include a shaft 1032 and an attachment portion 1034 with a protrusion 1036 extending out from the attachment portion 1034. The protrusion 1036 may have a round or ball shape.

Figure 26:
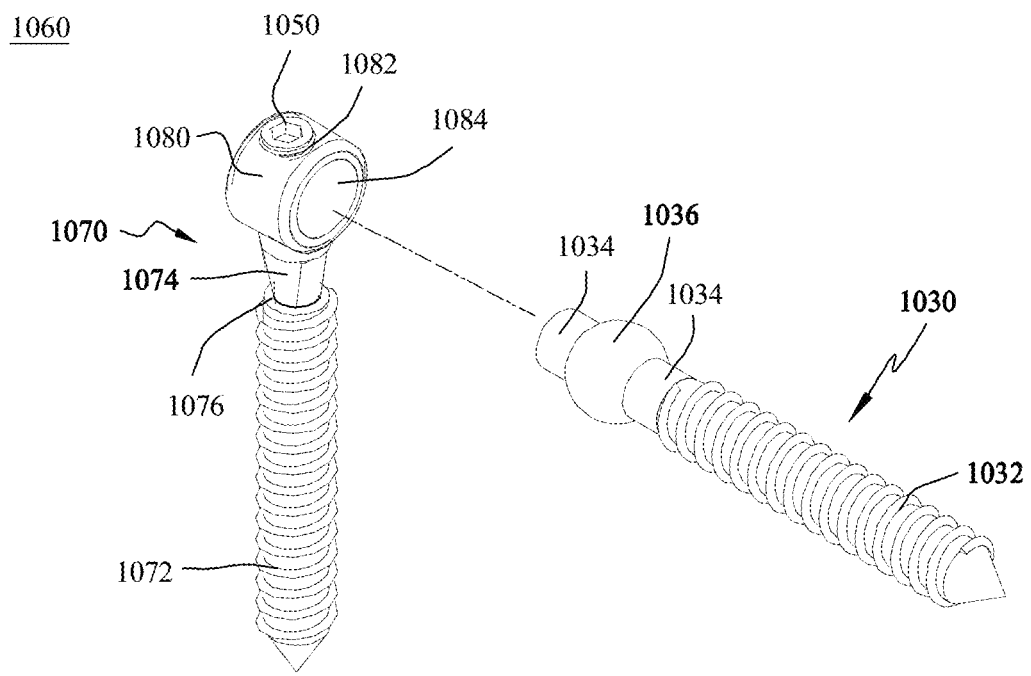
FIG. 26 is an exploded perspective view of the single level fusion system of FIG. 25, in accordance with an aspect of the present invention.
Figure 27:
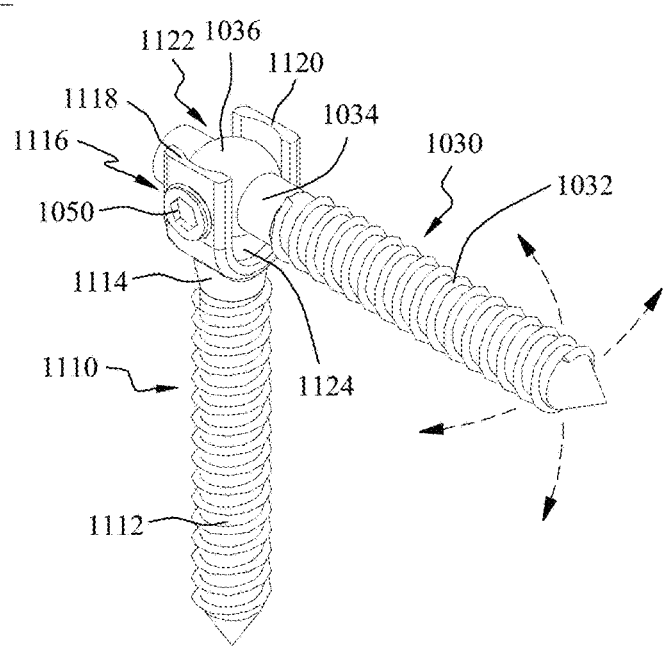
FIG. 27 is a perspective view of yet another single level fusion system, in accordance with an aspect of the present invention.
Figure 28:
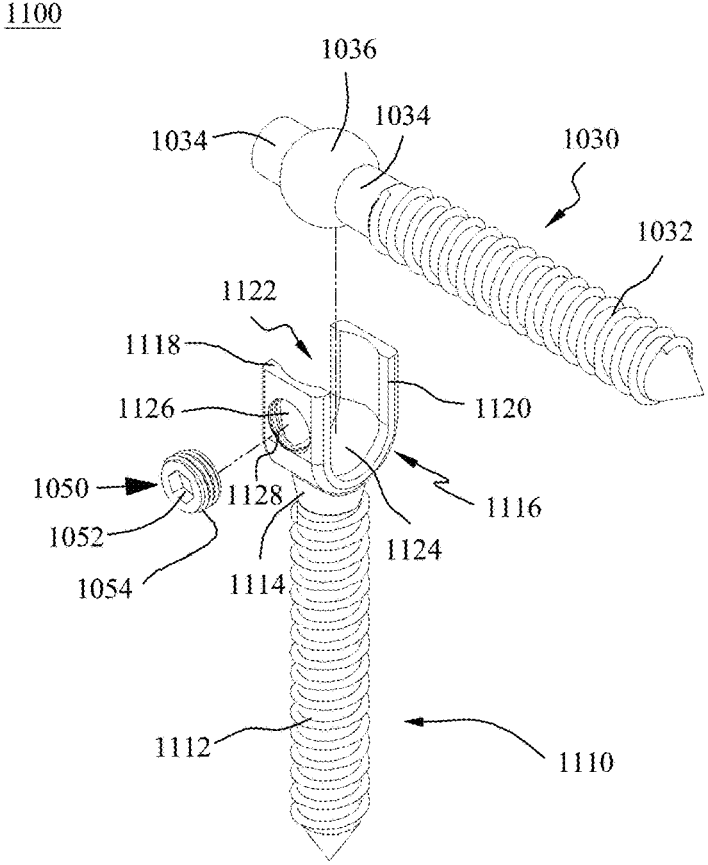
FIG. 28 is an exploded perspective view of the single level fusion system of FIG. 27, in accordance with an aspect of the present invention.
Figure 29:
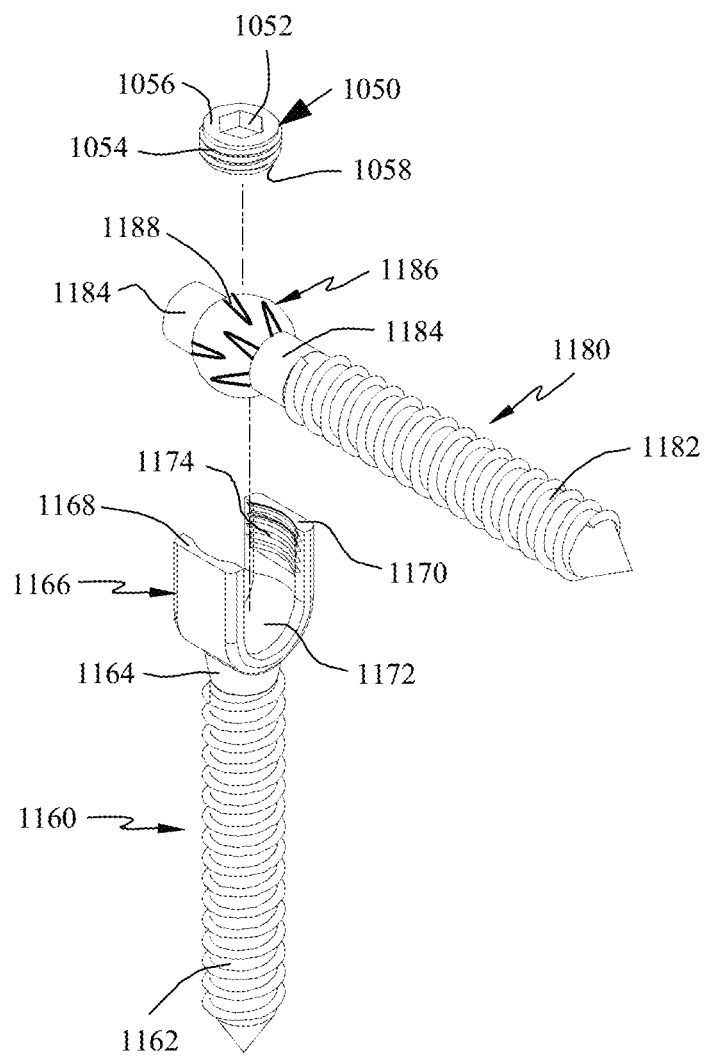
FIG. 29 is an exploded perspective view of another single level fusion system, in accordance with an aspect of the present invention.

As shown in FIGS. 22-30 and 38 and more specifically in FIGS. 28 and 29, the set screw 1050 may include a top surface 1056 and a bottom surface 1058. The set screw 1050 may also include a tool engagement opening 1052 extending into the set screw 1050 from the top surface 1056 toward the bottom surface 1058. In addition, the set screw 1050 may include threads 1054 on the exterior surface extending from the top surface 1056 to the bottom surface 1058. It is also contemplated that the set screw 1050 may be replaced with a ratcheting mechanism (not shown) that allows for the second fastener 1030 to pass into the opening 1026 in the first fastener 1010 in a first direction, but prevents the second fastener 1030 from moving through the opening 1026 in a second reverse direction.

To assemble the single level fusion device 1000, the attachment portion 1034 of the second fastener 1030 may be inserted into the opening 1026 of the head 1020 of the first fastener 1010. The attachment portion 1034 may be inserted until the protrusion 1036 is positioned within the opening 1026. Once inserted, the second fastener 1030 may be rotated slightly within the head 1020 of the first fastener 1010. Then, a set screw 1050 may be inserted into the first opening 1022 to secure the protrusion 1036 within the opening 1026 of the first fastener 1010 to secure the first fastener 1010 in a desired position with respect to the second fastener 1030. Additional rotation of the first fastener 1010 with respect to the second fastener 1030 may then be achieved for insertion into a patient by rotating the first and second fasteners 1010, 1030 at the hinge member 1024.

Figure 25:
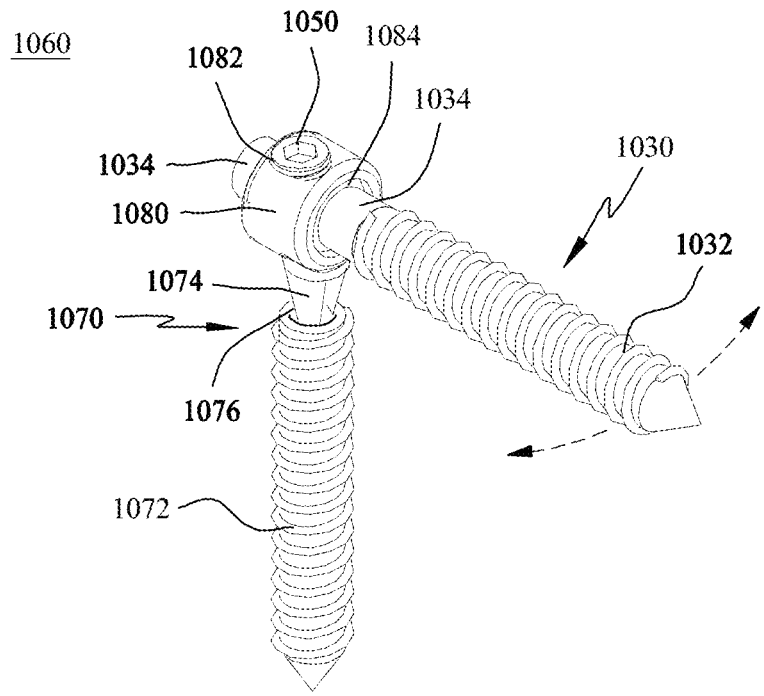
FIG. 25 is a perspective view of another embodiment of a single level fusion system, in accordance with an aspect of the present invention.

FIGS. 25-26 illustrate another single level fusion device 1060. The single level fusion device 1060 includes a first fastener 1070 and a second fastener 1030. The first fastener 1070 may include a shaft 1072, a neck 1074 attached to the shaft 1072 at a connection point 1076, and a head 1080 coupled to the neck 1074 at a position opposite the shaft 1072. The neck 1074 may be tapered from the head 1080 to the shaft 1072. In addition, the neck 1074 may be fixed. The shaft 1072 may be threaded along the entire length or only along a portion of the length. The head 1080 may include a first opening 1082 and a second opening 1084. The first opening 1082 may extend from the exterior surface of the head 1080 into the second opening 1084. The first opening 1082 may be threaded for receiving a set screw 1050. The second opening 1084 may extend entirely through the head 1080. The second fastener 1030 and the set screw 1050 are described in greater detail above and will not be described again here for brevity sake. It is also contemplated that the set screw 1050 may be replaced with a ratcheting mechanism (not shown) that allows for the second fastener 1030 to pass into the opening 1084 in the first fastener 1070 in a first direction but prevents the second fastener 1030 from moving through the opening 1084 in a second reverse direction.

To assemble the single level fusion device 1060, the attachment portion 1034 of the second fastener 1030 may be inserted into the opening 1084 of the head 1080 of the first fastener 1070. The attachment portion 1034 may be inserted until the protrusion 1036 is positioned within the opening 1084. Once inserted the second fastener 1030 may be rotated slightly within the head 1080 of the first fastener 1070. Then, a set screw 1050 may be inserted into the first opening 1082 to secure the protrusion 1036 within the opening 1084 of the first fastener 1070 to secure the first fastener 1070 in a desired position with respect to the second fastener 1030.

Referring now to FIGS. 27-28, a single level fusion device 1100 may include a first fastener 1110 and a second fastener 1030. The first fastener 1110 may include a shaft 1112, a head 1116, and a neck 1114 connecting the shaft 1112 and the head 1116. The shaft 1112 may be threaded, for example, along its entire length or along only a portion of the length. The head 1116 may include a first arm 1118, a second arm 1120, and a passageway 1122 extending between the first arm 1118 and the second arm 1120. The first arm 1118 and second arm 1120 each have an interior surface formed by the passageway 1122. The passageway 1122 also forms a base 1124 near the bottom of the head 1116. The base 1124 may be, for example, curved. The first arm 1118 and second arm 1120 may be shaped, for example, curved, to match the shape of the attachment portion 1034 of the second fastener 1030. In addition, the first fastener 1110 may include an opening 1126 with threads 1128 for receiving a set screw 1050. The second fastener 1030 and set screw 1050 are described in greater detail above and will not be described again here for brevity sake.

To assemble the single level fusion device 1100, the attachment portion 1034 of the second fastener 1030 may be inserted into the passageway 1122 of the head 1116 of the first fastener 1110. The attachment portion 1034 may be inserted until the protrusion 1036 is positioned within the passageway 1122. Once inserted, the second fastener 1030 may be rotated slightly within the head 1116 of the first fastener 1160. Then a set screw 1050 may be inserted into the opening 1126 to secure the protrusion 1036 within the passageway 1122 of the first fastener 1110 to secure the first fastener 1110 in a desired position with respect to the second fastener 1030.

An alternative embodiment of a single level fusion device 1150 is shown in FIG. 29 and includes a first fastener 1160, a second fastener 1180, and a set screw 1050. The first fastener 1160 may include a shaft 1162, a head 1166, and a neck 1164 connecting the shaft 1162 and the head 1166. The shaft 1162 may be threaded, for example, along its entire length or along only a portion of the length. The head 1166 may include a first arm 1168, a second arm 1170 opposite the first arm 1168 forming a passageway. The first arm 1168 and second arm 1170 may be connected by a base 1172 near the bottom of the head 1166. The base 1172 may be, for example, curved. The first arm 1168 and second arm 1170 may be shaped, for example, curved, to match the shape of the attachment portion 1034 of the second fastener 1030. In addition, the first arm 1168 and second arm 1170 may include threads 1174 on the interior surface extending from the top surface of the head 1166 down toward the base 1172.

The second fastener 1180, as shown in FIG. 29, may include a shaft 1182 and an attachment portion 1184 with a protrusion 1186 extending out from the attachment portion 1184. The protrusion 1186 may have a round or ball shape. The protrusion 1186 may include a plurality of openings 1188 to make the protrusion 1186 deformable. The openings 1188 create a collapsible or crushable construct 1186 that crimps down onto the threads 1174 in the head 1166 of the first fastener 1160 to secure the second fastener 1180 to the first fastener 1160 as the set screw 1050 is inserted.

To assemble the single level fusion device 1150, the attachment portion 1184 of the second fastener 1180 may be inserted into the head 1166 of the first fastener 1160. The attachment portion 1184 may be inserted until the protrusion 1186 is positioned between the first arm 1168 and the second arm 1170. Once inserted the second fastener 1180 may be rotated slightly within the head 1166 of the first fastener 1160 to reach a desired position. Then a set screw 1050 may be inserted into the head 1166 between the first arm 1168 and the second arm 1170 to secure the protrusion 1186 within the head 1166 of the first fastener 1160 to secure the first fastener 1160 in a desired position with respect to the second fastener 1180. The plurality of openings 1188 in the protrusion 1186 allow the protrusion 1186 to be deformed when a set screw 1050 is inserted.

Figure 30:
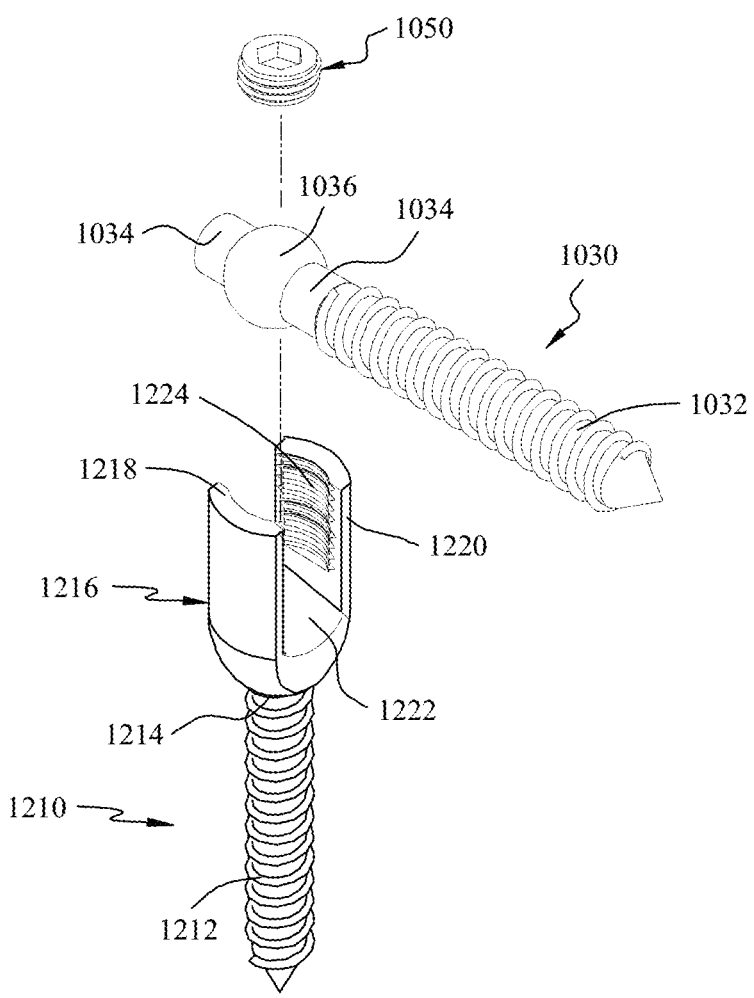
FIG. 30 is an exploded perspective view of yet another single level fusion system, in accordance with an aspect of the present invention.

FIG. 30 illustrates a single level fusion device 1200 and includes a first fastener 1210, a second fastener 1030, and a set screw 1050. The first fastener 1210 may include a shaft 1212, a head 1216, and a neck 1214 connecting the shaft 1212 and the head 1216. The shaft 1212 may be threaded, for example, along its entire length or along only a portion of the length. The head 1216 may include a first arm 1218, a second arm 1220 opposite the first arm 1218 forming a passageway. The length of the first arm 1218 and second arm 1220 may be longer as shown although the arms 1218, 1220 may be longer or shorter than the length of the arms 1218, 1220 shown. The first arm 1218 and second arm 1220 may be connected by a base 1222 near the bottom of the head 1216. The base 1222 may be, for example, curved. The first arm 1218 and second arm 1220 may be shaped, for example, curved, to match the shape of the attachment portion 1034 of the second fastener 1030, specifically to match the protrusion 1036. In addition, the first arm 1218 and second arm 1220 may include threads 1224 on the interior surface extending from the top surface of the head 1216 down toward the base 1222. The second fastener 1030 and set screw 1050 are described in greater detail above and will not be described again here for brevity sake.

To assemble the single level fusion device 1200, the attachment portion 1034 of the second fastener 1030 may be inserted into the head 1216 of the first fastener 1210. The attachment portion 1034 may be inserted until the protrusion 1036 is positioned between the first arm 1218 and the second arm 1220. Once inserted the second fastener 1030 may be rotated slightly within the head 1216 of the first fastener 1210. Then a set screw 1050 may be inserted into the head 1216 between the first arm 1218 and the second arm 1220 to secure the protrusion 1036 within the head 1216 of the first fastener 1210 to secure the first fastener 1210 in a desired position with respect to the second fastener 1030.

The fasteners 1010, 1030, 1070, 1110, 1160, 1180, and 1210 may be cannulated through the center of the shafts along a longitudinal axis to enable insertion over a guide wire, k-wire, pin, or the like to assist with insertion into the patient.

A method for inserting the single level fusion system 1000, 1060, 1100, 1150, 1200 of FIGS. 22-30 into a patient may include cutting a small incision in the patient, for example, a 3 cm incision. Next, the fascia is cut and muscles are split in line of the fibers to expose the patient's vertebrae. Once the vertebrae are exposed, an image guidance or fluoroscopy device may be used to insert a first fastener or pedicle screw 1010, 1070, 1110, 1160, 1210 into a first pedicle of a first vertebra. Also using an image guidance or fluoroscopy device, a second fastener or pedicle screw 1030, 1180 may then be inserted through the head 1020, 1080, 1116, 1166, 1216 of the first fastener 1010, 1070, 1110, 1160, 1210 and into an adjacent second pedicle of a second vertebra. The first fasteners 1010, 1070, 1110, 1160, 1210 may have a variable angled neck 1024 or a fixed neck 1074, 1114, 1164, 1214. The fasteners 1010, 1070, 1110, 1160, 1210, 1030, 1180 may be inserted using a guide wire if they are cannulated or free hand. A locking mechanism, for example, a set screw 1050 may be inserted into the head 1020, 1080, 1116, 1166, 1216 of the first fastener 1010, 1070, 1110, 1160, 1210 and tightened down to secure the second fastener 1030, 1180 to the first fastener 1010, 1070, 1110, 1160, 1210. The locking mechanism may be inserted, for example, from the side of the heads of fasteners 1010, 1070, 1110, 1160, 1210, as shown in FIGS. 22-28, or from the top of the heads of the fasteners 1010, 1070, 1110, 1160, 1210, as shown in FIGS. 29-30. Finally, the patient's incision may be closed.

Figure 31:
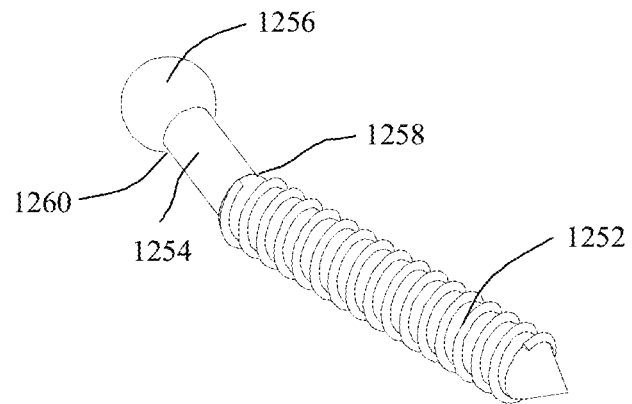
FIG. 31 is a perspective view of a fastener for a single level fusion system, in accordance with an aspect of the present invention.

A fastener 1250 is shown in FIG. 31. The fastener 1250 includes a threaded shaft 1252, a neck 1254, and a head 1256. The threaded shaft 1252 is coupled to the neck 1254 at connection 1258 which angles the threaded shaft 1252 with respect to the neck 1254. The head 1256 is coupled to the neck 1254 at connection 1260.

Figure 32:
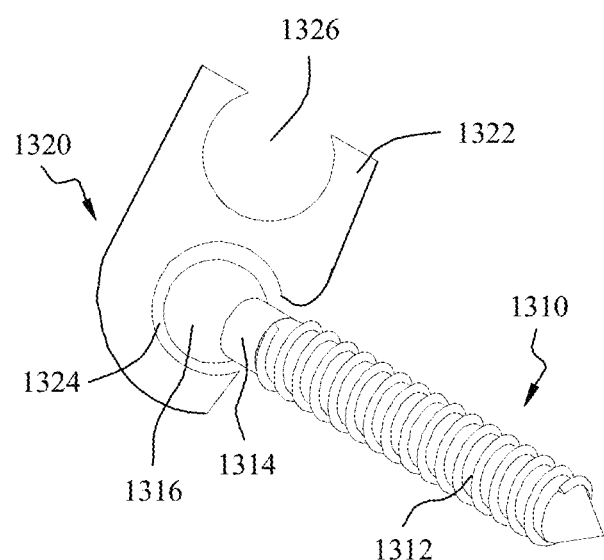
FIG. 32 is a side perspective view of another fastener for a single level fusion system, in accordance with an aspect of the present invention.

Referring now to FIG. 32, a fastener assembly 1300 is shown and includes a fastener 1310 and a coupling mechanism 1320. The fastener 1310 may include a shaft 1312, a neck 1314, and a head 1316. The neck 1314 is positioned between and couples the head 1316 to the shaft 1312. The coupling mechanism 1320 may include a body 1322 with a first opening 1324 and a second opening 1326. The body 1322 may have, for example, a generally rectangular or oval shape. The first opening 1324 may be positioned relatively perpendicular to the second opening 1326. The first opening 1324 may receive the head 1316 of the fastener 1310 and the second opening 1326 may receive an end of a second fastener, for example, second fastener 1030, 1180, 1250, 1430, or 1510.

Figure 33:
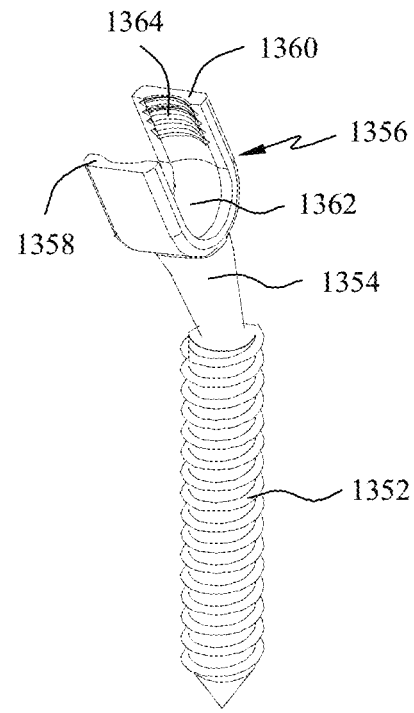
FIG. 33 is a perspective view of yet another fastener for a single level fusion system, in accordance with an aspect of the present invention.

Another fastener 1350 is shown in FIG. 33. The fastener 1350 may include a shaft 1352, a neck 1354, and a head 1356. The neck 1354 is positioned between the shaft 1352 and the head 1356 and may the neck 1354 may extend out of the shaft 1352 at either a straight or angled position to arrange the head 1356 either in line or angled with respect to the shaft 1352. The head 1356 may include a first arm 1358, a second arm 1360 positioned opposite the first arm 1358, and a base 1362 connecting the first arm 1358 and the second arm 1360. The base 1362 may have an interior surface that is, for example, planar or curved in either a concave or convex shape. The interior surface of the first arm 1358 and the second arm 1360 may each include a threaded portion 1364 for receiving a set screw, such as, set screw 160, 260, 350, 750, 850, and 1050.

Referring now to FIGS. 34-37, a single level fusion device 1400 is shown. The single level fusion device 1400 may include a first fastener 1410, a second fastener 1430, and a screw 1450. The first fastener 1410 may include a shaft 1412, a head 1416, and a neck 1414 connecting the shaft 1412 and the head 1416. The shaft 1412 may be threaded, for example, along its entire length or along only a portion of the length. The head 1416 may include a first arm 1418, a second arm 1420 opposite the first arm 1418 forming a passageway. The first arm 1418 and second arm 1420 may be connected by a base 1422 near the bottom of the head 1416. The base 1422 may be, for example, curved. The first arm 1418 and second arm 1420 may be shaped, for example, curved, to match the shape of the protrusion 1436 of the attachment portion 1434 of the second fastener 1430. In addition, the first arm 1418 and second arm 1420 may have a knurled or roughened surface 1424 on the interior surface extending from the top surface of the head 1416 down toward the base 1422. It is also contemplated that in an alternative embodiment, the first fastener 1410 could be a fastener 1010 or 1070 including a head 1020 or 1080.

Figure 34:
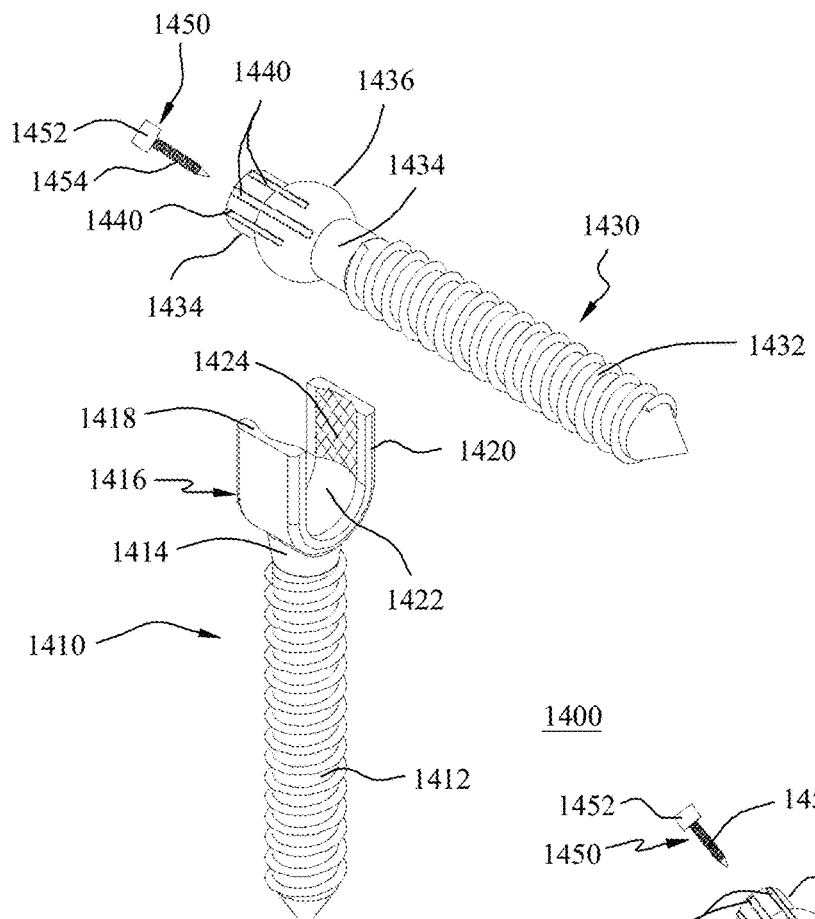
FIG. 34 is an exploded perspective view of another single level fusion system, in accordance with an aspect of the present invention.
Figure 35:
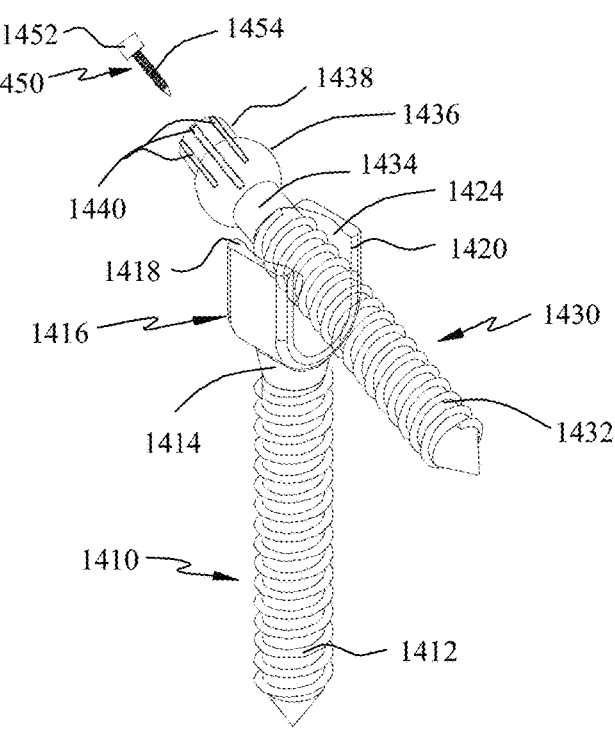
FIG. 35 is a partially exploded view of the single level fusion system of FIG. 34, in accordance with an aspect of the present invention.

The second fastener 1430, as shown in FIGS. 34-35, may include a shaft 1432 and an attachment portion 1434 with a protrusion 1436 extending out from the attachment portion 1434. The protrusion 1436 may have a round or ball shape. The attachment portion 1434 may include openings 1440 extending from a first end of the second fastener 1430 into the protrusion 1436 to make the protrusion 1436 deformable. The screw 1450 includes a head 1452 and a shaft 1454 extending out of the bottom of the head 1452. The shaft 1454 of the screw 1450 may be sized and shaped to be inserted into one of the openings 1440 in the attachment portion 1434 and protrusion 1436 to expand the protrusion 1436 to couple the second fastener 1430 to the first fastener 1410.

To assemble the single level fusion device 1400, the attachment portion 1434 of the second fastener 1430 may be inserted into the head 1416 of the first fastener 1410. The attachment portion 1434 may be inserted until the protrusion 1436 is positioned between the first arm 1418 and the second arm 1420. Once inserted the second fastener 1430 may be rotated slightly within the head 1416 of the first fastener 1410. Then, the screw 1450 may be inserted into the attachment portion 1434 and protrusion 1436 to secure the protrusion 1436 within the head 1416 of the first fastener 1410 to secure the first fastener 1410 in a desired position with respect to the second fastener 1430. The plurality of openings 1440 in the protrusion 1436 allow the protrusion 1436 to be deformed when a screw 1450 is inserted.

The fasteners 1410, 1430 may be cannulated through the center of the shafts along a longitudinal axis of the fasteners 1410, 1430 to enable insertion over a guide wire, k-wire, pin, or the like to assist with insertion into the patient.

A method for inserting the single level fusion system 1400 of FIGS. 34-37 into a patient may include cutting a small incision in the patient, for example, a 3 cm incision. Next, the fascia is cut and muscles are split in line of the fibers to expose the patient's vertebrae. Once the vertebrae are exposed, an image guidance or fluoroscopy device may be used to insert a first fastener or pedicle screw 1410 into a first pedicle of a first vertebra. The image guidance or fluoroscopy device may also be used to insert a second fastener or pedicle screw 1430 through the head 1416 of the first fastener 1410 and into an adjacent pedicle of a second vertebra. The first fasteners 1410 may have a variable angled neck or a fixed neck. The fasteners 1410, 1430 may be inserted using a guide wire if the fasteners 1410, 1430 are cannulated or free hand. A locking mechanism, for example, a screw 1450 may be used to secure the first fastener 1410 and second fastener 1430. The screw 1450 may be inserted into the end of the attachment portion 1434 of the second fastener 1430 to expand the protrusion 1436 of the second fastener 1430 and secure the second fastener 1430 within the head 1416 of the first fastener 1410. Finally, the patient's incision may be closed.

Figure 36:
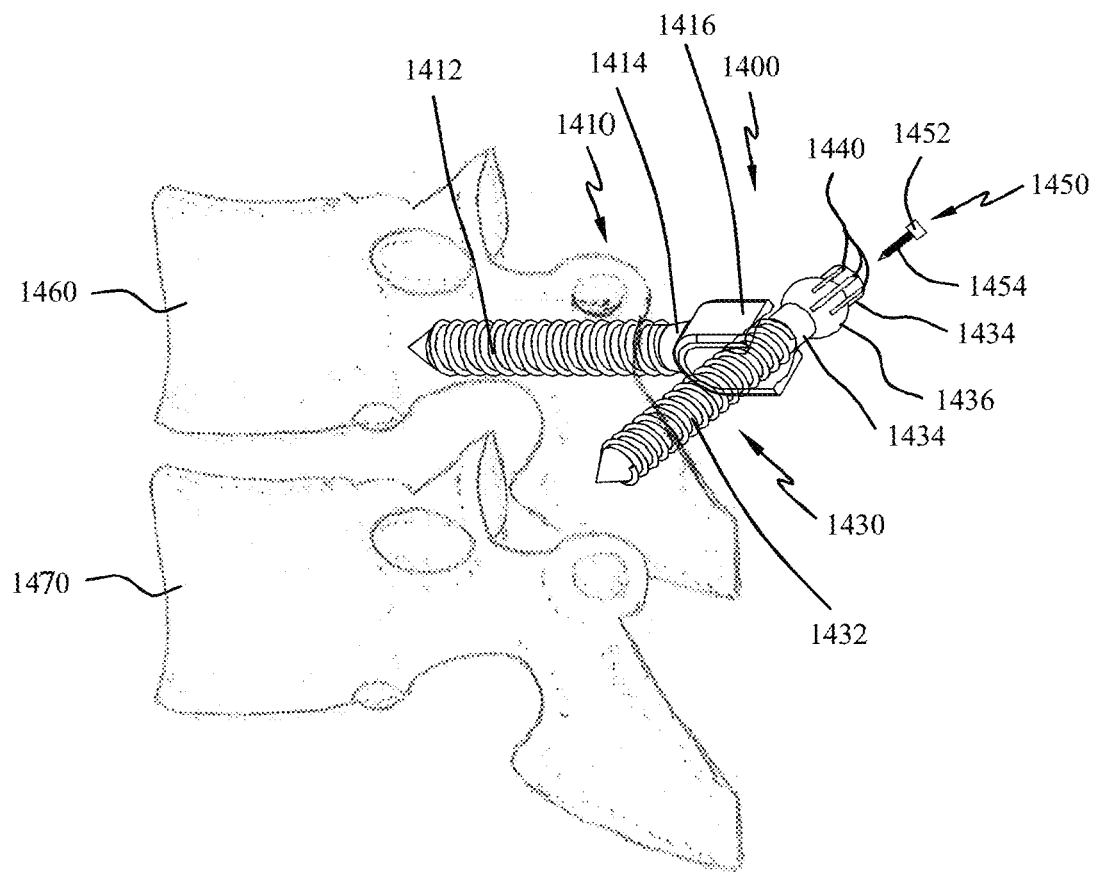
FIG. 36 is a perspective view of the single level fusion system of FIG. 34 partially inserted into two vertebrae, in accordance with an aspect of the present invention.

As shown in FIG. 36, the method of inserting the single level fusion system 1400 may further include inserting the first fastener 1410 into a first vertebra 1460. The second fastener 1430 may then be inserted through the head 1416 of the first fastener 1410 and into the second vertebra 1470. Once the protrusion 1436 of the second fastener 1430 is positioned in the head 1416 of the first fastener 1410 and the first fastener 1410 and second fastener 1430 are in the desired position within the first and second vertebrae 1460, 1470, then the screw 1450 may be inserted. The screw 1450 may be inserted into the openings 1440 in the second fastener 1430 to expand the protrusion 1436 in the head 1416 to secure the second fastener 1430 to the first fastener 1410.

Figure 37:
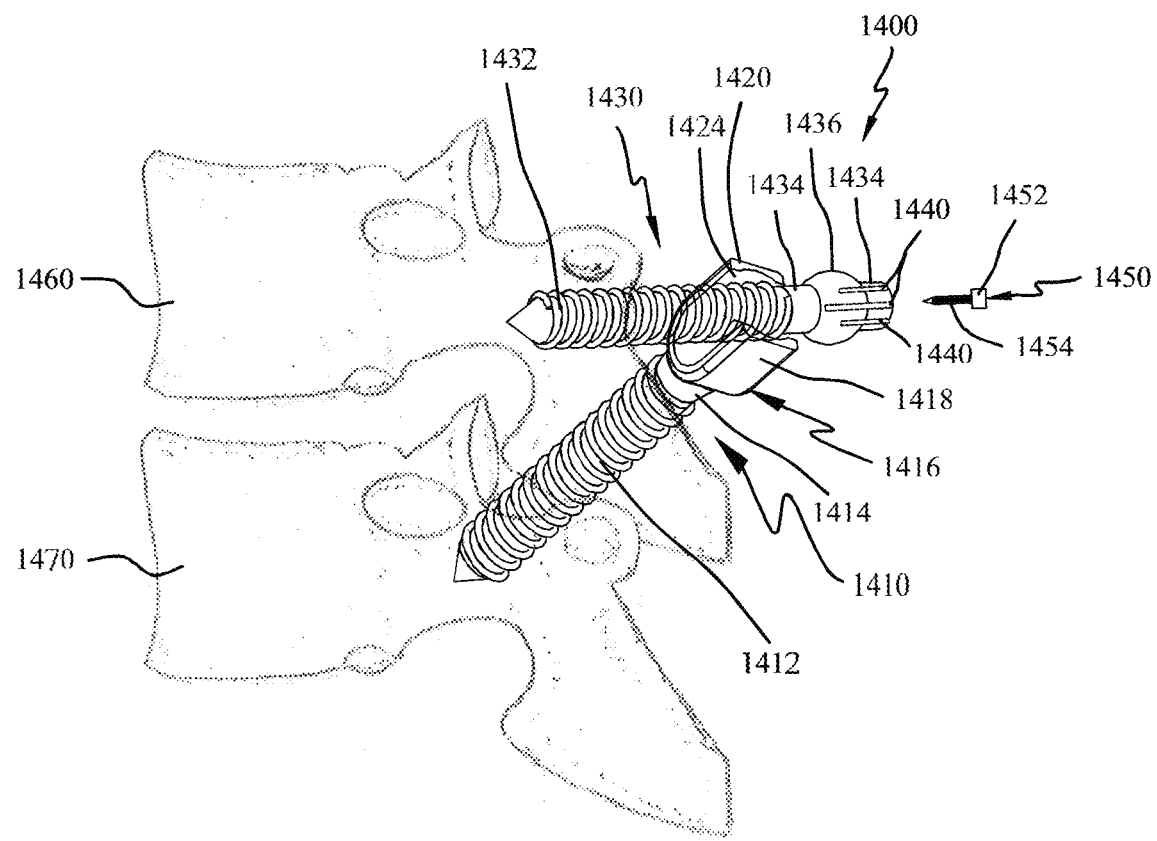
FIG. 37 is a perspective view of the single level fusion system of FIG. 34 partially inserted into two vertebrae, in accordance with an aspect of the present invention.

As shown in FIG. 37, the method of inserting the single level fusion system 1400 may alternatively include inserting the first fastener 1410 into the second vertebra 1470. The second fastener 1430 may then be inserted through the head 1416 of the first fastener 1410 and into the first vertebra 1460. Once the protrusion 1436 of the second fastener 1430 is positioned in the head 1416 of the first fastener 1410 and the first fastener 1410 and second fastener 1430 are in the desired position within the second and first vertebrae 1470, 1460, respectively, then the screw 1450 may be inserted. The screw 1450 may be inserted into the openings 1440 in the second fastener 1430 to expand the protrusion 1436 in the head 1416 to secure the second fastener 1430 to the first fastener 1410.

Figure 38:
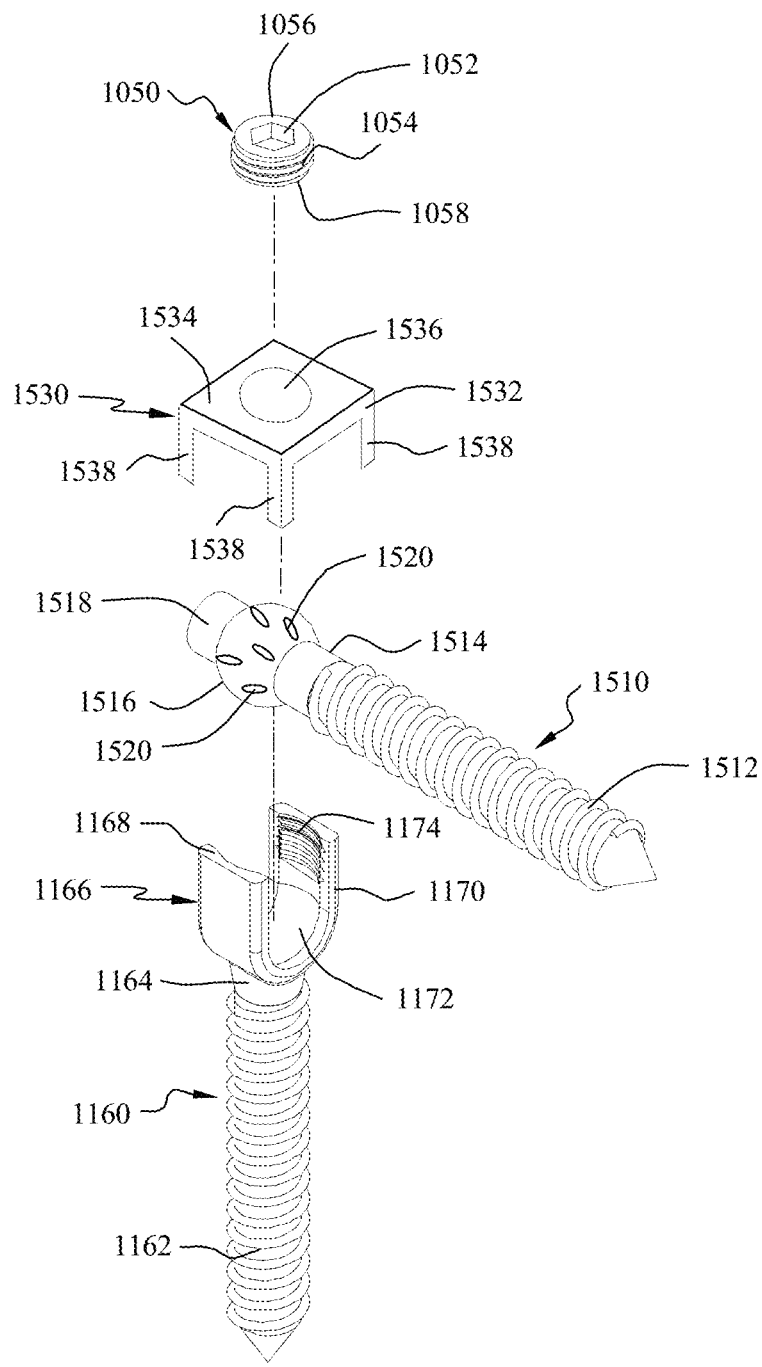
FIG. 38 is a perspective view of another embodiment of a single level fusion system, in accordance with an aspect of the present invention.
Figure 39:
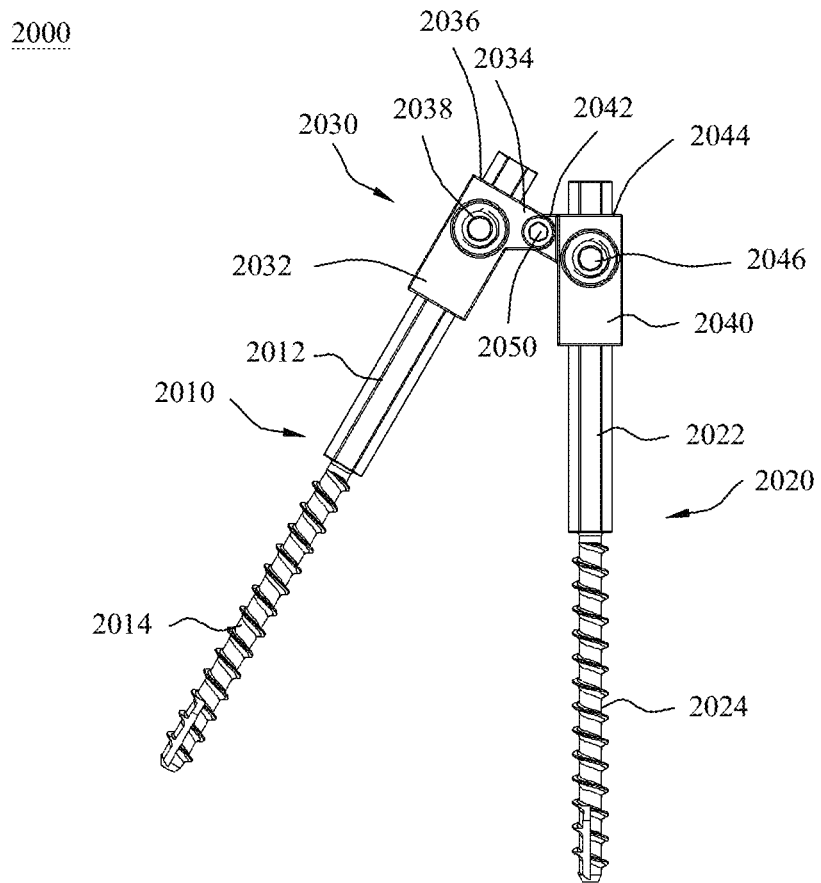
FIG. 39 is a front view of another embodiment of a single level fusion system, in accordance with an aspect of the present invention.
Figure 40:
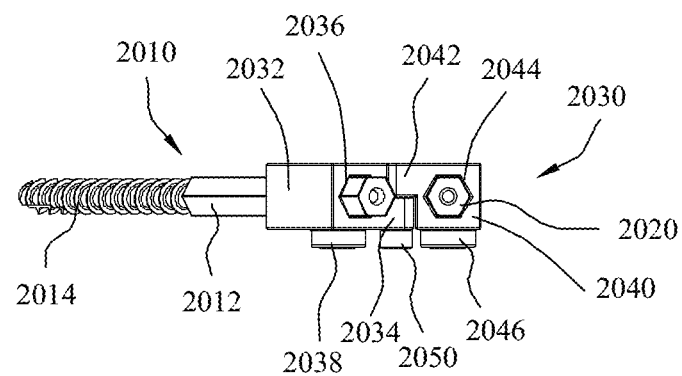
FIG. 40 is a top view of the single level fusion system of FIG. 39, in accordance with an aspect of the present invention.
Figures 41, 42:
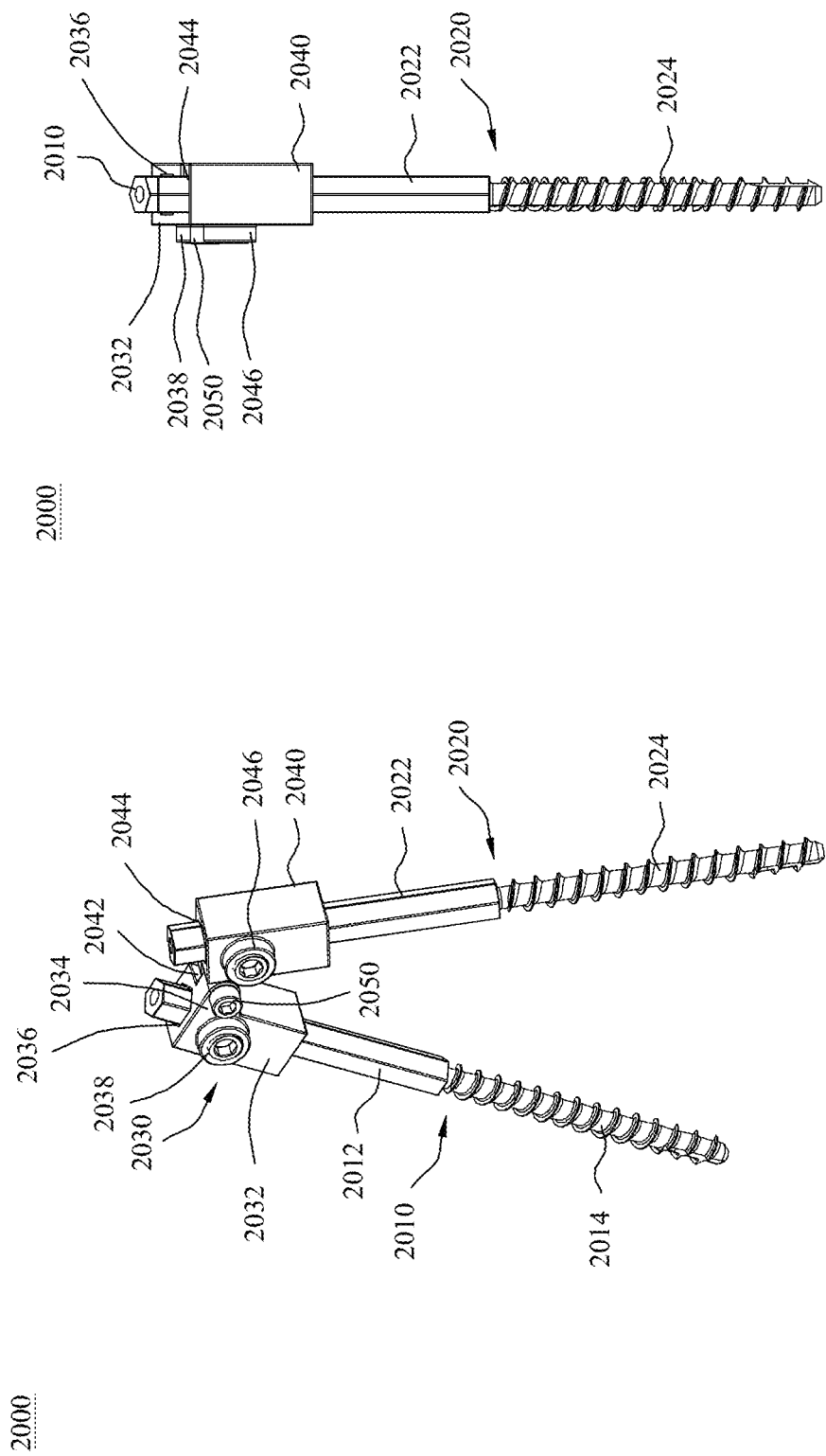
FIG. 41 is a perspective view of the single level fusion system of FIG. 39, in accordance with an aspect of the present invention.
FIG. 42 is a side view of the single level fusion system of FIG. 39, in accordance with an aspect of the present invention.

A single level fusion device 1500 is shown in FIG. 38. The single level fusion device 1500 may include a first fastener 1160, a second fastener 1510, a securement member 1530, and a set screw 1050. The first fastener 1160 and the set screw 1050 are describe above in greater detail and will not be described again here for brevity sake. The second fastener 1510 may include a shaft 1512, an attachment portion 1514 with a protrusion 1516 extending out from the attachment portion 1514, and an end portion 1518 extending out from the protrusion 1516. The protrusion 1516 may have a round or ball shape. The protrusion 1516 may include a plurality of openings 1520 to make the protrusion 1516 deformable. The securement member 1530 may include a base 1532 with a top surface 1534 and four legs 1538 extending down from the top surface 1534. The top surface 1534 may also include an opening 1536 extending through the top surface for receiving the protrusion 1516.

To assemble the single level fusion device 1500, the protrusion 1516 of the second fastener 1510 may be inserted into the head 1166 of the first fastener 1160. The protrusion 1516 may be positioned between the first arm 1168 and the second arm 1170. Once inserted the second fastener 1510 may be rotated slightly within the head 1166 of the first fastener 1160 until the desired position is achieved. Then, the securement member 1530 may be inserted into the head 1166 between the arms 1168, 1170 and positioned over the protrusion 1516. Next, a set screw 1050 may be inserted into the head 1166 between the first arm 1168 and the second arm 1170 to secure the securement member 1530 and the protrusion 1516 within the head 1166 of the first fastener 1160 to secure the first fastener 1160 in a desired position with respect to the second fastener 1510. The plurality of openings 1520 in the protrusion 1516 allow the protrusion 1516 to be deformed when a set screw 1050 is inserted.

The fasteners 1160, 1510 may be cannulated through the center of the shafts along a longitudinal axis of the fasteners 1160, 1510 to enable insertion over a guide wire, k-wire, pin, or the like to assist with insertion into the patient.

A method for inserting the single level fusion system 1500 of FIG. 38 into a patient may include cutting a small incision in the patient, for example, a 3 cm incision. Next, the fascia is cut and muscles are split in line of the fibers to expose the patient's vertebrae. Once the vertebrae are exposed, an image guidance or fluoroscopy device may be used to insert a first fastener or pedicle screw 1160 into a first pedicle of a first vertebra. The image guidance or fluoroscopy device may also be used to insert a second fastener or pedicle screw 1510 through the head 1166 of the first fastener 1160 and into an adjacent pedicle of a second vertebra. The first fastener 1160 may have a variable angled neck or a fixed neck. The fasteners 1160, 1510 may be inserted using a guide wire if the fasteners 1160, 1510 are cannulated or free hand. A locking mechanism, for example, a set screw 1050 may be used to secure the first fastener 1160 and second fastener 1510. The locking mechanism may also optionally include a securement member 1530 which may be inserted over the second fastener 1510 before inserting the set screw 1050. The set screw 1050 may be inserted into the head 1166 of the first fastener 1160 to secure the protrusion 1516 of the second fastener 1510. Finally, the patient's incision may be closed.

Referring now to FIGS. 39-42, a rodless single level fusion system 2000 is shown. The system 2000 may include a first fastener or screw 2010, a second fastener or screw 2020, and a connector 2030. The connector 2030 may be configured to receive the first fastener 2010 and the second fastener 2020. The first fastener 2010 may be, for example, a screw, straight wire, or curved wire. The first fastener 2010 may include a first portion 2012 and a second portion 2014. The first portion 2012 may have a, for example, hexagonal shape and may extend from a first end of the screw 2010 to a position near the midpoint. The second portion 2014 may be, for example, threaded and may extend from a second end of the screw 2010 to a position near the midpoint. The second fastener 2020 may be, for example, a screw, straight wire, or curved wire. The second fastener 2020 may include a first portion 2022 and a second portion 2024. The first portion 2022 may have a, for example, hexagonal shape and may extend from a first end of the screw 2020 to a position near the midpoint. The second portion 2024 may be, for example, threaded and may extend from a second end of the screw 2020 to a position near the midpoint.

The connector 2030 may include a first member 2032, a second member 2040, and a locking pin 2050 coupling the first member 2032 and a second member 2040. The terms "locking pin", "locking mechanism", "locking means", "fixation mechanism" and "fixation means" may be used interchangeably herein to refer to a structure that secures the first member 2032 with respect to the second member 2040 at a desired angulation. The first member 2032 may include a first hinge connector 2034 with an opening (not shown) to receive the locking pin 2050. The first member 2032 may also include a channel 2036 extending along the longitudinal axis of the first member 2032 for receiving the first fastener 2010. The first member 2032 may further include an opening (not shown) for receiving a first securement member 2038 to secure the first fastener 2010 to the first member 2032 at a desired length. The opening may extend from an exterior surface of the first member 2032 into the channel 2036. The second member 2040 may include a second hinge connector 2042 with an opening (not shown) to receive the locking pin 2050. The first hinge connector 2034 and second hinge connector 2042 are hingedly coupled together by the locking pin 2050. The second member 2040 may also include a channel 2044 extending along the longitudinal axis of the second member 2040 for receiving the second fastener 2020. The second member 2040 may further include an opening (not shown) for receiving a second securement member 2046 to secure the second fastener 2020 to the second member 2040 at a desired length. The opening may extend from an exterior surface of the second member 2040 into the channel 2044. The first hinge connector 2034 is rotatably coupled to the second hinge connector 2042 by the locking pin 2050 and allows for the first member 2032 and the second member 2040 to rotate with respect to each other about the locking pin 2050. In addition, the locking pin 2050 may secure the connector 2030 at a desired angle between the first member 2032 and the second member 2040. The angle between the first member 2032 and the second member 2040 may be, for example, approximately 0° to 60°. More preferably, the locking pin 2050 may be secured at angles of, for example, 15°, 20°, 25°, 30°, 35°, 40°, 45°, 50°, 55° and 60° between the first member 2032 and the second member 2040.

Figure 43:
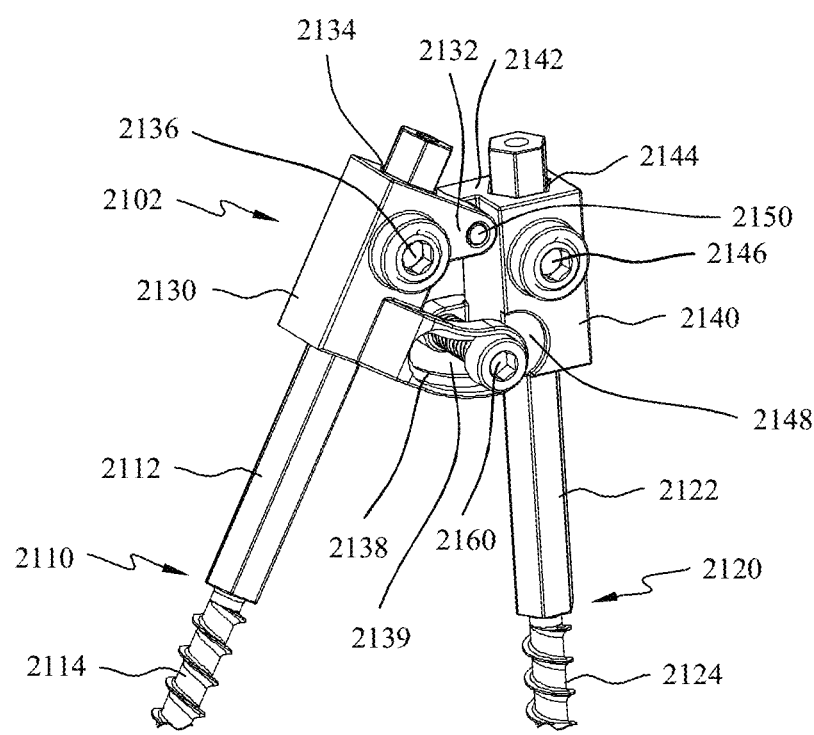
FIG. 43 is a perspective view of another embodiment of a single level fusion system, in accordance with an aspect of the present invention.

Referring now to FIG. 43, a rodless single level fusion system 2100 is shown. The system 2100 may include a first fastener or screw 2110, a second fastener or screw 2120, and a connector 2102. The connector 2102 may be configured to receive the first fastener 2110 and the second fastener 2120. The first fastener 2110 may be, for example, a screw, straight rod, or curved rod, which may be smooth or fluted. The first fastener 2110 may include a first portion 2112 and a second portion 2114. The first portion 2112 may have a, for example, hexagonal shape and may extend from a first end of the screw 2110 to a position near the midpoint. The second portion 2114 may be, for example, threaded and may extend from a second end of the screw 2110 to a position near the midpoint. The second fastener 2120 may be, for example, a screw, straight rod, or curved rod, which may be smooth or fluted. The second fastener 2120 may include a first portion 2122 and a second portion 2124. The first portion 2122 may have a, for example, hexagonal shape and may extend from a first end of the screw 2120 to a position near the midpoint. The second portion 2124 may be, for example, threaded and may extend from a second end of the screw 2120 to a position near the midpoint.

The connector 2102 may include a first member 2130, a second member 2140, a hinge pin 2150 coupling the first member 2130 and a second member 2140, and a locking mechanism 2160. The first member 2130 may include a first hinge connector 2132 with an opening (not shown) to receive the hinge pin 2150. The first member 2130 may also include an opening 2134 extending along the longitudinal axis of the first member 2032 for receiving the first fastener 2110. The first member 2130 may further include an opening (not shown) for receiving a first securement member 2136 to secure the first fastener 2110 to the first member 2130 at a desired length. The first member 2130 may also include an adjustment member 2138 with an opening 2139. The adjustment member 2138 may be, for example, curved or arced. The opening 2139 may be sized, for example, to receive a locking mechanism 2160. The connector 2102 provides for angular adjustment, in multiple planes and includes a locking mechanism to provide rigid fixation between bone screws 2110, 2120 to address variability in patient anatomy.

The second member 2140 may include a second hinge connector 2142 with an opening (not shown) to receive the pin 2150, as shown in FIG. 43. The first hinge connector 2132 and second hinge connector 2142 are hingedly coupled together by the pin 2150. The second member 2140 may also include an opening 2144 extending along the longitudinal axis of the second member 2140 for receiving the second fastener 2120. The second member 2140 may further include an opening (not shown) for receiving a second securement member 2146 to secure the second fastener 2120 to the second member 2140 at a desired length. The second member 2140 may also include a groove 2148 shaped to receive the adjustment member 2138. The second member 2140 may also include a securement member (not shown) for the locking mechanism 2160 to be secured to in order to lock the connector 2102 at a desired angle between the first fastener 2110 and the second fastener 2120. The first hinge connector 2132 is rotatably coupled to the second hinge connector 2142 by the locking pin 2150 and allows for the first member 2130 and the second member 2140 to rotate with respect to each other about the hinge pin 2150.

Figure 44:
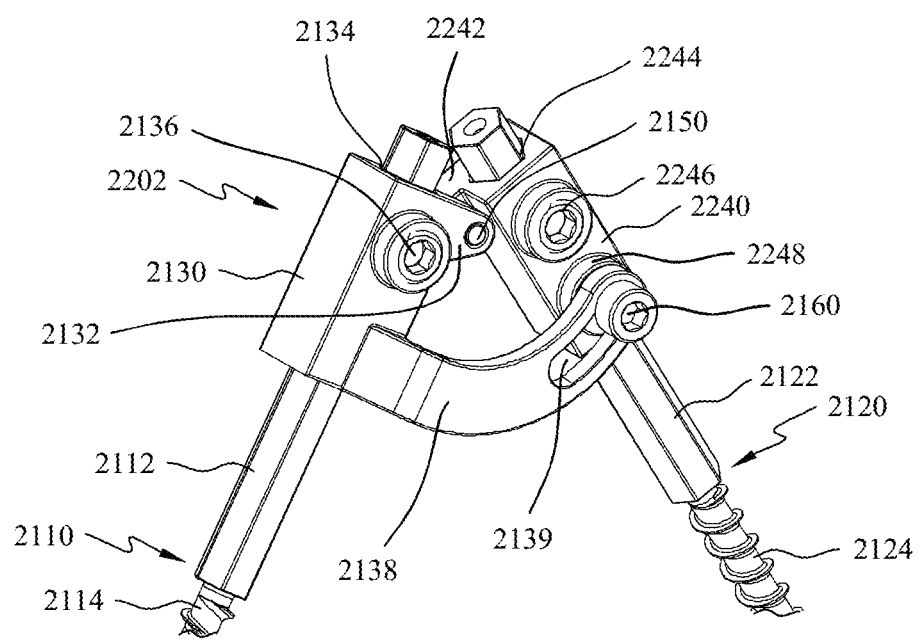
FIG. 44 is a perspective view of yet another embodiment of a single level fusion system, in accordance with an aspect of the present invention.

Referring now to FIG. 44, a single level fusion system 2200 is shown. The system 2200 is an alternative embodiment of the system 2100 of FIG. 43. The system 2200 may include a first fastener or screw 2110, a second fastener or screw 2120, and a connector 2202. The connector 2202 may be configured to receive the first fastener 2110 and the second fastener 2120. The first and second fasteners 2110, 2120 are of the type described above and will not be described again here for brevity sake. The connector 2202 may include a first member 2130, a second member 2240, a hinge pin 2150 coupling the first member 2130 and a second member 2240, and a locking mechanism 2160. The first member 2130 may be of the type described above with reference to FIG. 43 and will not be described again here for brevity sake. The connector 2202 provides for angular adjustment, in multiple planes and includes a locking mechanism to provide rigid fixation between bone screws 2110, 2120 to address variability in patient anatomy.

The second member 2240 may include a second hinge connector 2242 with an opening (not shown) to receive the pin 2150, as shown in FIG. 44. The first hinge connector 2132 and second hinge connector 2242 are hingedly coupled together by the pin 2150. The second member 2240 may also include an opening 2244 extending along the longitudinal axis of the second member 2240 for receiving the second fastener 2120. The second member 2240 may further include an opening (not shown) for receiving a second securement member 2246 to secure the second fastener 2120 to the second member 2240 at a desired length. The second member 2240 may also include an opening 2248 for receiving the locking mechanism 2160. The locking mechanism 2160 may extend through the opening 2139 in the adjustment member 2138 in order to lock the connector 2102 at a desired angle between the first fastener 2110 and the second fastener 2120. The first hinge connector 2132 is rotatably coupled to the second hinge connector 2242 by the locking pin 2150 and allows for the first member 2130 and the second member 2240 to rotate with respect to each other about the hinge pin 2150.

Figure 45:
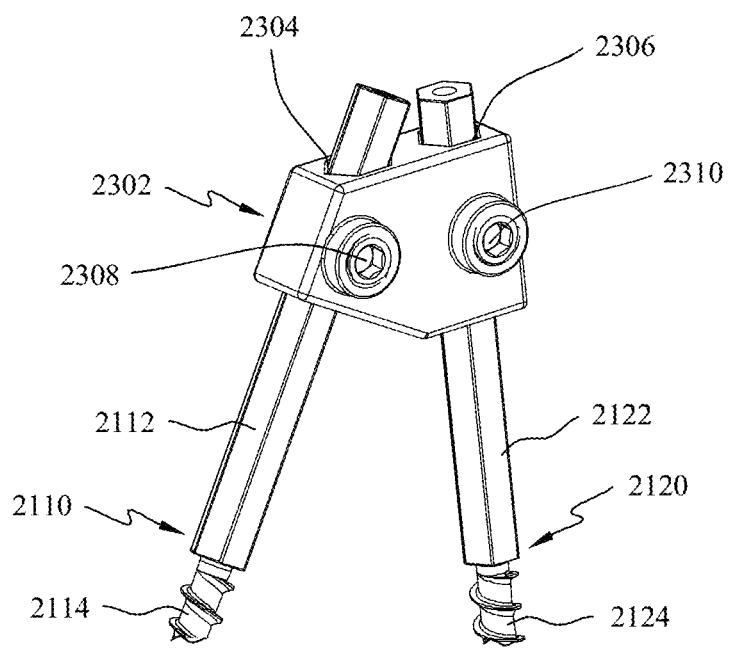
FIG. 45 is a perspective view of a further embodiment of a single level fusion system, in accordance with an aspect of the present invention.

Another single level fusion system 2300 is shown in FIG. 45. The single level fusion system 2300 may include a first fastener or screw 2110, a second fastener or screw 2120, and a connector 2302. The connector 2302 may be configured to receive the first fastener 2110 and the second fastener 2120. The first and second fasteners 2110, 2120 are of the type described above and will not be described again here for brevity sake. The connector 2302 may be, for example, a one piece connector. The connector 2302 may include a first opening 2304 extending from a top portion through to a bottom portion of the connector 2302. The first opening 2304 may be sized and shaped to receive the first fastener 2110. The connector 2302 may also include a second opening 2306 extending from a top portion through to a bottom portion generally along a longitudinal axis of the connector 2302. The second opening 2306 may be sized and shaped to receive the second fastener 2120. The first opening 2304 may be spaced apart from the second opening 2306. The connector 2302 may also include an opening (not shown) for receiving a first securement member 2308 to secure the first fastener 2110 in the first opening 2304 at a desired length. The connector 2302 may further include an opening (not shown) for receiving a second securement member 2310 to secure the second fastener 2120 in the second opening 2306 at a desired length.

Figure 46:
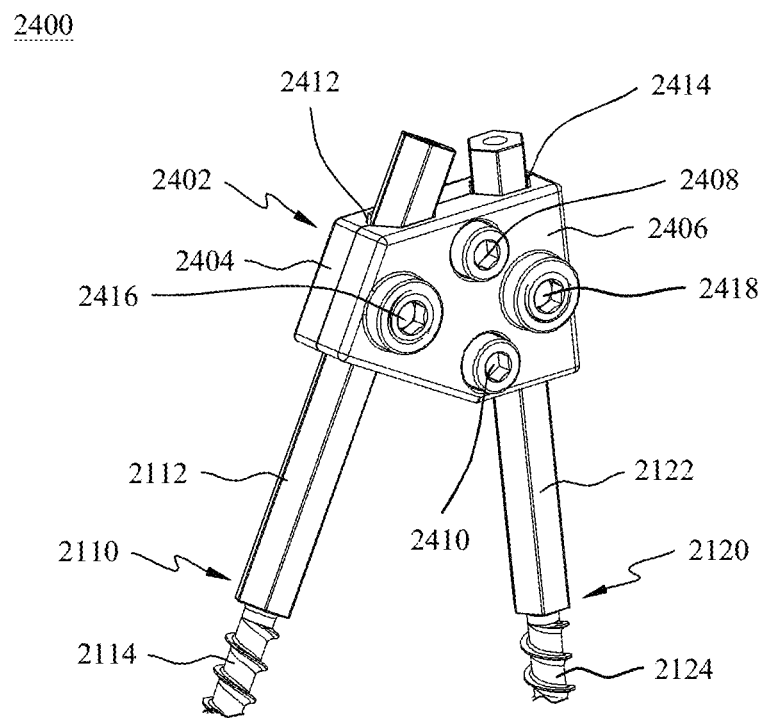
FIG. 46 is a perspective view of yet another embodiment of a single level fusion system, in accordance with an aspect of the present invention.

FIG. 46 shows yet another single level fusion system 2400. The single level fusion system 2400 may include a first fastener or screw 2110, a second fastener or screw 2120, and a connector 2402. The connector or clamp connector 2402 may be configured to receive the first fastener 2110 and the second fastener 2120. The first and second fasteners 2110, 2120 are of the type described above and will not be described again here for brevity sake. The connector 2402 may be, for example, a two piece connector. The connector 2402 may include a first member 2404 and a second member 2406. The first and second members 2404, 2406 may be coupled together with a first fastener 2408 and a second fastener 2410. The connector 2402 may also include a first opening 2412 extending from a top portion through to a bottom portion of the connector 2402. The first opening 2412 may be sized and shaped to receive the first fastener 2110. The connector 2402 may also include a second opening 2414 extending from a top portion through to a bottom portion generally along a longitudinal axis of the connector 2402. The second opening 2414 may be sized and shaped to receive the second fastener 2120. The first opening 2412 may be spaced apart from the second opening 2414. The connector 2402 may also include an opening (not shown) for receiving a first securement member 2416 to secure the first fastener 2110 in the first opening 2412 at a desired length. The connector 2402 may further include an opening (not shown) for receiving a second securement member 2418 to secure the second fastener 2120 in the second opening 2414 at a desired length.

The connectors 2302 and 2402, as shown in FIGS. 45-46, may be, for example, non-pivoting locking blocks already positioned at the desired angle of correction.

A method of using the single level fusion system 2000 is shown in FIGS. 44-46. The method may include preparing a patient's vertebrae for insertion of the single level fusion system 2000. Next, a first fastener 2010 may be inserted into a first vertebra 2060 and a second fastener 2020 may be inserted into a second vertebra 2070, as shown in FIG. 44. The first and second fasteners 2010, 2020 are inserted to allow for divergence in only one dimension. As shown in FIG. 45, the posterior-anterior view shows one trajectory for the first and second fasteners 2010, 2020 in which divergence is only in one dimension, for example, cephalad-caudal. The cephalad directed fastener 2010, 2020 may pass through one cortical layer and may end in the pedicle. The caudal directed fastener 2010, 2020 may pass through the thick cortical layer of the superior facet of the inferior vertebra and end in the pedicle. Once the fasteners 2010, 2020 are inserted into the vertebrae, the proximal ends of the fasteners 2010, 2020 may be connected by the connector 2030. Referring now to FIG. 46, the axial view shows the trajectory through the facet and pedicle for the trajectory drawn in FIG. 45. After the connector 2030 is coupled to the first and second fasteners 2010, 2020, the connector 2030 may be secured at the desired angle between the first and second fasteners 2010, 2020. Finally, the patient's incision may be closed.

Figure 47:
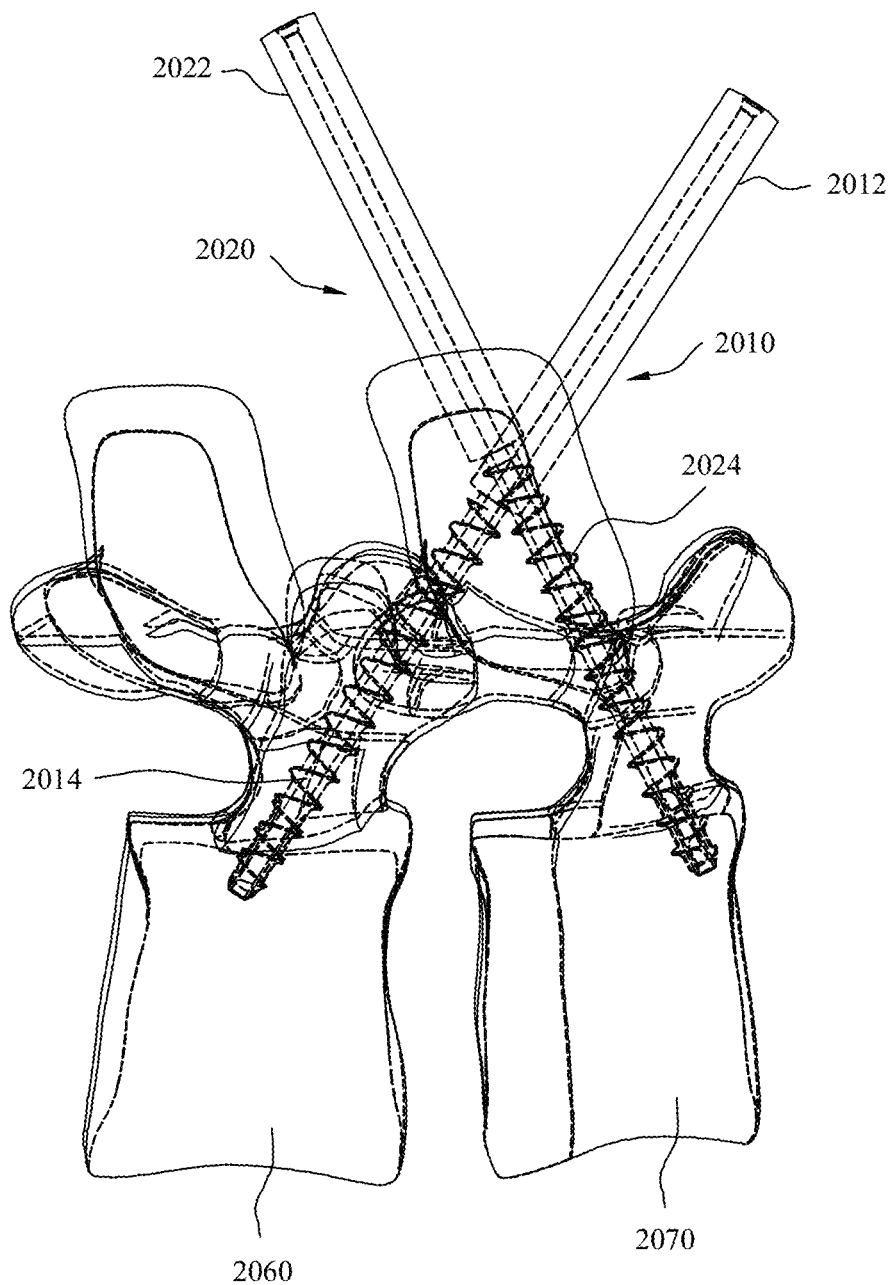
FIG. 47 is a lateral view of the single level fusion system of FIG. 39 partially inserted into two vertebrae, in accordance with an aspect of the present invention.
Figure 48:
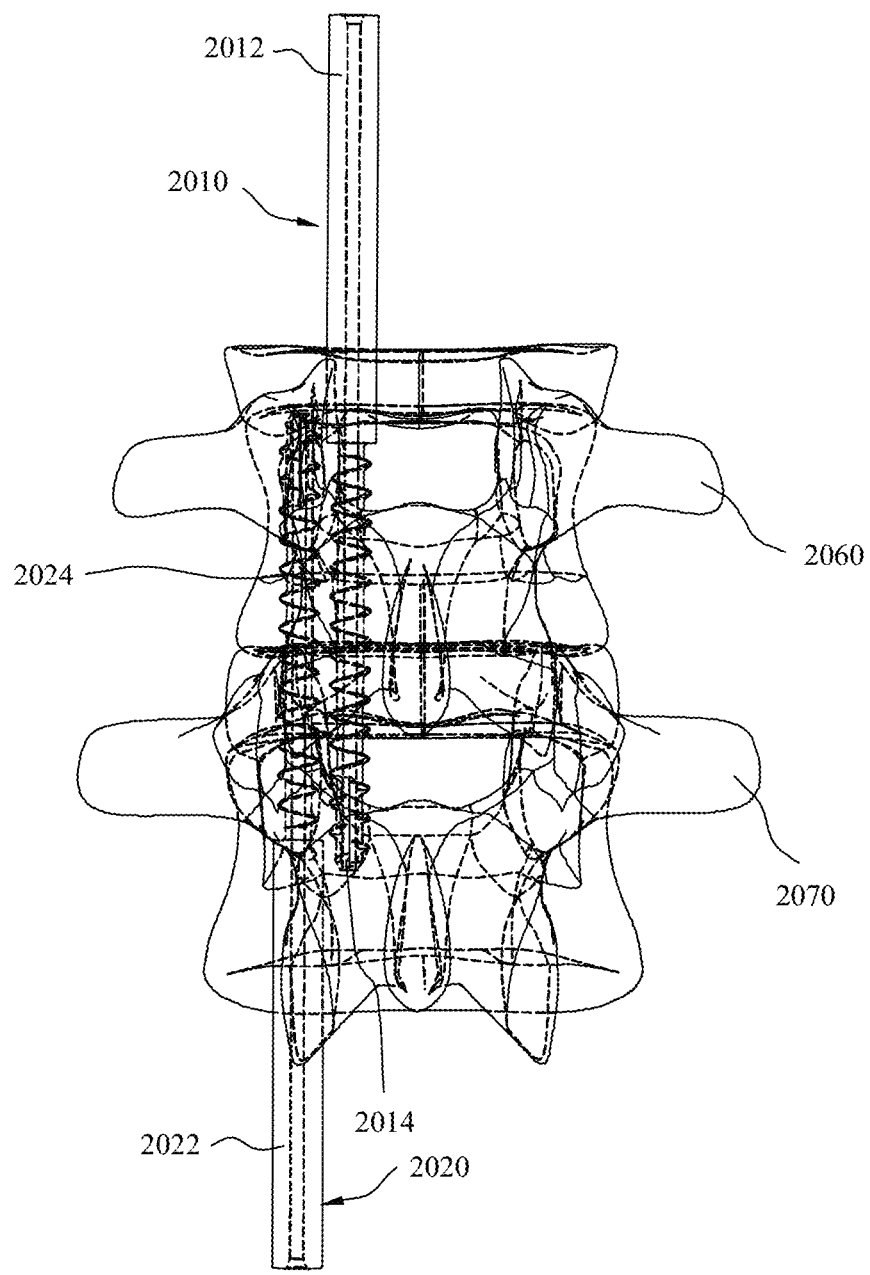
FIG. 48 is a posterior view of the two vertebrae and single level fusion system of FIG. 47, in accordance with an aspect of the present invention.
Figure 49:
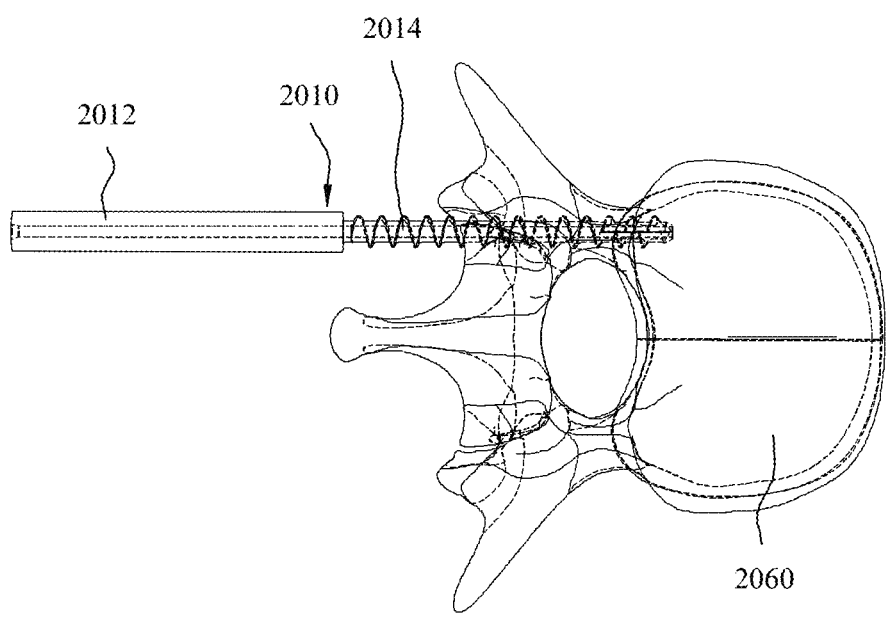
FIG. 49 is an axial view of the two vertebrae and single level fusion system of FIG. 47, in accordance with an aspect of the present invention.
Figure 50:
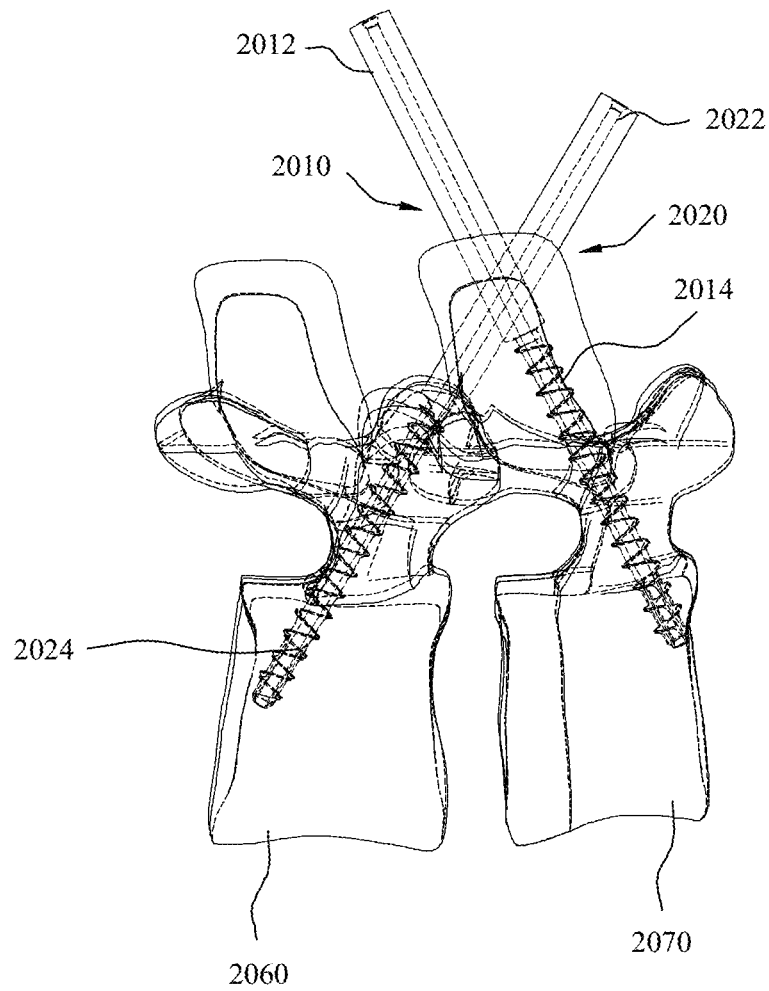
FIG. 50 is another lateral view of the single level fusion system of FIG. 39 inserted into two vertebrae, in accordance with an aspect of the present invention.
Figure 51:
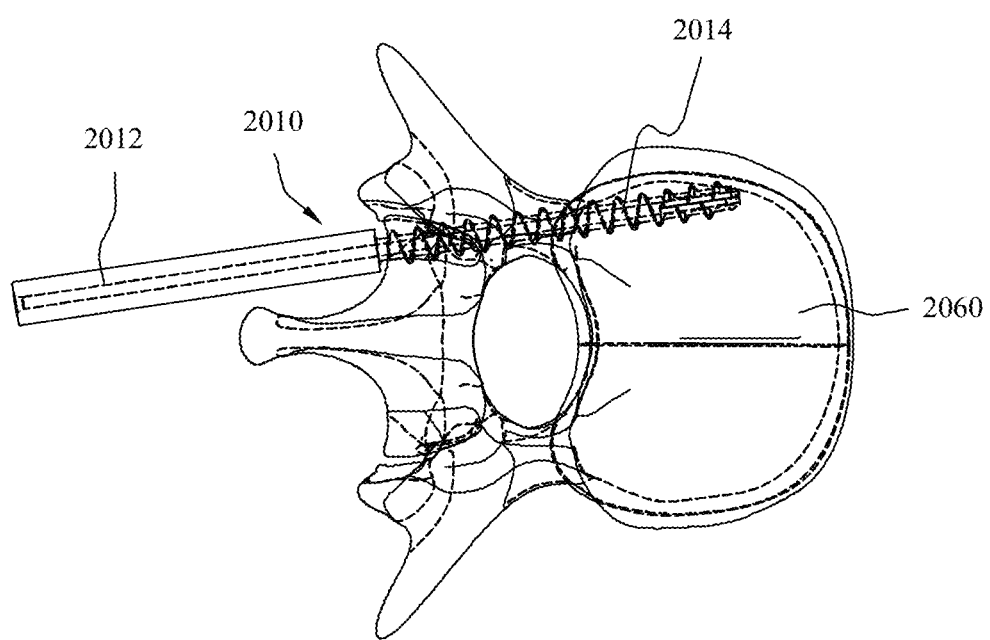
FIG. 51 is a side view of the two vertebrae and single level fusion system of FIG. 50, in accordance with an aspect of the present invention.

Another method of using the single level fusion system 2000 is shown in FIGS. 47-48. The method may include preparing a patient's vertebrae for insertion of the single level fusion system 2000. Next, a first fastener 2010 may be laterally inserted into a first vertebra 2060 and a second fastener 2020 may be laterally inserted into a second vertebra 2070, as shown in FIG. 47. The first and second fasteners 2010, 2020 are inserted to allow for divergence in two dimensions to increase pull-out strength. The fastener 2010, 2020 inserted in the cephalad direction engages two cortices as well as the pedicle, while the fastener 2010, 2020 inserted in the caudal direction engages four cortices. There are two trajectories for the first and second fasteners 2010, 2020 in which divergence is in multiple directions, cephalad-caudal, medial-lateral and lateral right or lateral left. The cephalad directed fasteners 2010, 2020 may pass through two cortices as well as the pedicle. The fasteners 2010, 2020 inserted in a cephalad, medial-lateral, and lateral right or left direction achieves three dimensional stability. Alternatively, caudal directed fasteners 2010, 2020 engage four cortical surfaces as well as the pedicle to also achieve three dimensional stability. Referring now to FIG. 48, the axial view shows the medial lateral trajectory through the medial facet, pedicle, and lateral vertebral cortex of the vertebrae 2060, 2070. After the connector 2030 is coupled to the first and second fasteners 2010, 2020 the connector 2030 may be secured at the desired angle between the first and second fasteners 2010, 2020 and located lateral to the spinous process. Finally, the patient's incision may be closed.

As may be recognized by those of ordinary skill in the art based on the teachings herein, numerous changes and modifications may be made to the above-described and other embodiments of the present invention without departing from the scope of the invention. The fasteners, elongate members, and other components of the devices and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and systems may include more or fewer components or features than the embodiments as described and illustrated herein. For example, the components and features of FIGS. 1-21 may all be used interchangeably and in alternative combinations as would be modified or altered by one of skill in the art. In addition, the components and features of, for example, FIGS. 22-38 may all be used interchangeably and in alternative combinations as would be modified or altered by one of skill in the art. Accordingly, this detailed description of the currently-preferred embodiments is to be taken as illustrative, as opposed to limiting the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A single level fusion system, comprising:
   a first fastener assembly, comprising:
     a first fastener, comprising:
       a shaft;
       a head comprising:
          a first arm with a threaded portion on at least a portion of the first arm;
          a second arm with a threaded portion on at least a portion of the second arm;
          a passageway extending between the first arm and the second arm;
   a second fastener assembly, comprising:
     a second fastener comprising:
       a shaft;
       a head comprising:
          a first arm;
          a second arm; and at least one opening extending through at least a portion of the first arm and at least a portion of the second arm, wherein the at least one opening is tapered between a top surface of the head and the shaft; and an elongate member with a first end and a second end, wherein the elongate member couples the first fastener assembly to the second fastener assembly, and wherein the first end engages the first fastener assembly and the second end is hingedly connected to the at least one opening in the at least a portion of the first arm and the at least a portion of the second arm of the second fastener assembly.

2. The system of claim 1, wherein the first fastener assembly, further comprises:
a first set screw, wherein the first set screw removably couples to the first fastener.

3. The system of claim 2, wherein the first fastener further comprises:
a first interior surface with the threaded portion on at least a portion of the first interior surface;
a second interior surface with the threaded portion on at least a portion of the second interior surface;
a neck coupling the shaft to the head; and
wherein the first set screw engages the threaded portions of the first arm and the second arm to couple to the first fastener.

4. The system of claim 3, wherein a bottom surface of the first set screw engages a portion of the elongate member to secure the elongate member between the first fastener and the first set screw.

5. The system of claim 3, wherein the first arm includes a first extension tab forming a longer arm, wherein the second arm includes a second extension tab forming a longer arm, and wherein the first and second arms include a break off line to provide a break off point to shorten the arms by removing the first and second extension tabs.

6. The system of claim 2, wherein the at least one opening receives at least one hinge member, and wherein the at least one hinge member extends through the second end of the elongate member to hingedly couple the elongate member to the first arm and second arm of the head of the second fastener.

7. The system of claim 6, wherein the second fastener, further comprises:
a first threaded portion on at least a portion of an interior surface of the first arm; and
a second threaded portion on at least a portion of an interior surface of the second arm.

8. The system of claim 7, wherein the second fastener assembly further comprises:
a second set screw, and wherein the second set screw engages the first threaded portion of the first arm and the second threaded portion of the second arm to couple the second set screw to the second fastener.

9. The system of claim 8, wherein a bottom surface of the second set screw engages a portion of the elongate member to secure the elongate member between the second fastener and the second set screw.

10. The system of claim 6, wherein the second fastener, further comprises:
a first threaded portion positioned on an exterior of the first arm of the head; and
a second threaded portion positioned on an exterior of the second arm of the head.

11. The system of claim 10, wherein the second fastener assembly further comprises:

a second nut with an interior surface, wherein at least a portion of the interior surface is threaded, and wherein the threaded interior surface of the second nut engages the threaded portions of the first arm and the second arm of the head of the second to secure the fastener second nut to the second fastener; and wherein the second nut engages a portion of the elongate member to secure the elongate member between a base of the head of the second fastener and the second nut.

12. The system of claim 11, wherein the second end of the elongate member is opposite the first end; and
wherein a portion of the elongate member at the first end is at least one of round or polygonal and a portion of the elongate member at the second end is rectangular, and wherein the rectangular portion tapers into the at least one of round or polygonal portion between the first end and the second end of the elongate member.

13. The system of claim 11, wherein the second end of the elongate member is opposite the first end; and
wherein the elongate member comprises:
a first recess extending from a top surface of the elongate member toward a bottom surface between the first end and the second end; and
a second recess extending from the bottom surface of the elongate member toward the top surface between the first end and the second end.

14. The system of claim 11, wherein the first arm includes a first extension tab forming a longer arm, wherein the second arm includes a second extension tab forming a longer arm, and wherein the first and second arms include a break off line between the first and second arms and first and second extension tabs, respectively, to provide a break off point to shorten the arms by removing the first and second extension tabs.

15. The system of claim 1, wherein the first fastener assembly, comprises:
a first nut, wherein an interior surface of the first nut is threaded to secure the first nut to an exterior surface of the head of the first fastener.

16. The system of claim 15, wherein the at least one opening receives at least one hinge member, and wherein the at least one hinge member extends through the second end of the elongate member to hingedly couple the elongate member to the first arm and second arm of the head of the second fastener.

17. The system of claim 1, wherein the second end of the elongate member is opposite the first end; and
wherein a portion of the elongate member at the first end is at least one of round or polygonal and a portion of the elongate member at the second end is rectangular, and wherein the rectangular portion tapers into the at least one of round or polygonal portion between the first end and the second end of the elongate member.

18. The system of claim 1, wherein the second end of the elongate member is opposite the first end; and
wherein the elongate member further comprises:
a first recess extending from a top surface of the elongate member toward a bottom surface between the first end and the second end; and
a second recess extending from the bottom surface of the elongate member toward the top surface between the first end and the second end.

19. A method of assembling a single level fusion system, comprising:
obtaining a first fastener, a second fastener, and an elongate member;

wherein the first fastener comprises:
  a shaft;
  a head comprising:
    a first arm with a threaded portion on at least a portion of the first arm;
    a second arm with a threaded portion on at least a portion of the second arm;
    a passageway extending between the first arm and the second arm;
wherein the second fastener comprises:
  a shaft;
  a head comprising:
    a first arm;
    a second arm; and
    at least one opening extending through at least a portion of the first arm and at least a portion of the second arm, wherein the at least one opening is tapered between a top surface of the head and the shaft; and
wherein the elongate member has a first end and a second end;
inserting a hinge member through the opening in at least a portion of the first arm and at least portion of the second arm of the second fastener and an opening in at least a portion of the second end of the elongate member to hingedly couple the at least a portion of the elongate member to the second fastener; and
positioning the first end of the elongate member within the head of the first fastener; and
securing the first end of the elongate member to the first fastener with at least one of a set screw and a nut to couple the first fastener to the second fastener.

20. A surgical method for inserting a spinal fusion system, comprising:
exposing a patient's vertebrae;
obtaining the spinal fusion system, wherein the spinal fusion system comprises:
  a first fastener assembly, comprising:
    a first fastener, comprising:
      a shaft;
      a head comprising:
        a first arm with a threaded portion on at least a portion of the first arm;
        a second arm with a threaded portion on at least a portion of the second arm;
        a passageway extending between the first arm and the second arm;
  a second fastener assembly, comprising:
    a second fastener comprising:
      a shaft;
      a head comprising:
        a first arm;
        a second arm; and
        at least one opening extending through at least a portion of the first arm and at least a portion of the second arm, wherein the at least one opening is tapered between a top surface of the head and the shaft; and
  an elongate member with a first end and a second end;
coupling the elongate member of the spinal fusion system to the second fastener of the spinal fusion system, wherein the second end of the elongate member is hingedly connected to the at least one opening in the at least a portion of the first arm and the at least a portion of the second arm of the second fastener assembly;
inserting the first fastener of the spinal fusion system into a first vertebra;
inserting the second fastener into a second vertebra adjacent to the first vertebra;
engaging the elongate member with the first fastener, wherein the first end of the elongate member engages the first fastener; and
coupling the elongate member to the first fastener to couple the first fastener to the second fastener.

* * * * *